United States Patent
Durack et al.

(10) Patent No.: US 8,101,426 B2
(45) Date of Patent: Jan. 24, 2012

(54) SYSTEM AND METHOD FOR THE MEASUREMENT OF MULTIPLE FLUORESCENCE EMISSIONS IN A FLOW CYTOMETRY SYSTEM

(75) Inventors: Gary Durack, Urbana, IL (US); Jeremy Hatcher, Urbana, IL (US)

(73) Assignee: iCyt Mission Technology, Inc., Champaign, IL (US)

( * ) Notice: Subject to any disclaimer, the term of this patent is extended or adjusted under 35 U.S.C. 154(b) by 644 days.

(21) Appl. No.: 11/738,860

(22) Filed: Apr. 23, 2007

(65) Prior Publication Data

US 2008/0213915 A1 Sep. 4, 2008

Related U.S. Application Data

(60) Provisional application No. 60/892,716, filed on Mar. 2, 2007.

(51) Int. Cl.
*G01N 21/64* (2006.01)
*G01N 21/00* (2006.01)

(52) U.S. Cl. ............. 436/172; 436/164; 422/82.08; 422/82.05; 422/50; 422/68.1

(58) Field of Classification Search ........... 436/172, 436/164; 422/82.08, 82.05, 68.1, 50
See application file for complete search history.

(56) References Cited

U.S. PATENT DOCUMENTS

| | | |
|---|---|---|
| 3,920,983 A | 11/1975 | Schlafer et al. |
| 3,946,239 A | 3/1976 | Salzman et al. |
| 3,989,381 A | 11/1976 | Fulwyler |
| 4,188,543 A | 2/1980 | Brunsting et al. |
| 4,189,236 A | 2/1980 | Hogg et al. |
| 4,606,636 A | 8/1986 | Monin et al. |
| 4,802,768 A | 2/1989 | Gifford et al. |
| 4,871,249 A | 10/1989 | Watson |
| 5,066,133 A | 11/1991 | Brienza |
| 5,135,759 A | 8/1992 | Johnson |
| 5,270,548 A | 12/1993 | Steinkamp |
| 5,304,810 A | 4/1994 | Amos |
| 5,317,162 A | 5/1994 | Pinsky et al. |
| 5,418,371 A | 5/1995 | Aslund et al. |
| 5,430,541 A | 7/1995 | Sapp et al. |

(Continued)

FOREIGN PATENT DOCUMENTS

WO  WO 93/07471  4/1993

(Continued)

OTHER PUBLICATIONS

Jameson, David M.; Gratton, Enrico; Hall, Robert D., "The Measurement and Analysis of Heterogeneous Emissions by Multifrequency Phase and Modulation Fluorometry," Applied Spectroscopy Reviews, vol. 20, No. 1, 1984, pp. 55-106.

(Continued)

*Primary Examiner* — Christine T Mui
(74) *Attorney, Agent, or Firm* — Woodard, Emhardt, Moriarty, McNett & Henry LLP

(57) ABSTRACT

A system and method for the measurement of multiple fluorescence emissions in a flow cytometry system is disclosed where each excitation light source is modulated with a different frequency. A single detector is used to collect the fluorescent emissions excited by all light sources, and the emissions are segregated using Fourier Transform techniques. Systems and methods for the correction of inter-beam coincidence are also disclosed.

34 Claims, 14 Drawing Sheets

U.S. PATENT DOCUMENTS

| | | | |
|---|---|---|---|
| 5,471,299 | A | 11/1995 | Kaye et al. |
| 5,504,337 | A * | 4/1996 | Lakowicz et al. .......... 250/461.2 |
| 5,565,982 | A | 10/1996 | Lee et al. |
| 5,619,326 | A | 4/1997 | Takamatsu et al. |
| 5,624,847 | A | 4/1997 | Lakowicz et al. |
| 5,757,013 | A | 5/1998 | Groger et al. |
| 5,784,157 | A | 7/1998 | Gorfinkel et al. |
| 5,885,840 | A * | 3/1999 | Kamentsky et al. ............ 436/63 |
| 6,078,390 | A | 6/2000 | Bengtsson |
| 6,124,597 | A | 9/2000 | Shehada et al. |
| 6,149,867 | A | 11/2000 | Seidel et al. |
| 6,150,119 | A | 11/2000 | Kopf-Sill et al. |
| 6,323,474 | B1 | 11/2001 | Bacarella |
| 6,511,853 | B1 | 1/2003 | Kopf-Sill et al. |
| 6,528,801 | B1 | 3/2003 | Luryi et al. |
| 6,528,802 | B1 | 3/2003 | Koenig et al. |
| 6,592,822 | B1 | 7/2003 | Chandler |
| 6,660,149 | B1 | 12/2003 | Karger et al. |
| 6,683,314 | B2 | 1/2004 | Oostman, Jr. et al. |
| 6,813,017 | B1 * | 11/2004 | Hoffman et al. ............. 356/317 |
| 6,825,927 | B2 | 11/2004 | Goldman et al. |
| 6,919,044 | B1 | 7/2005 | Shibata et al. |
| 6,954,722 | B2 | 10/2005 | Parks et al. |
| 7,024,316 | B1 | 4/2006 | Ellison et al. |
| 7,371,517 | B2 | 5/2008 | Evans et al. |
| 7,723,116 | B2 | 5/2010 | Evans et al. |
| 7,758,811 | B2 | 7/2010 | Durack et al. |
| 2003/0016352 | A1 | 1/2003 | Goldman et al. |
| 2003/0020895 | A1 | 1/2003 | Bridges |
| 2003/0054558 | A1 | 3/2003 | Kurabayashi et al. |
| 2003/0068827 | A1 | 4/2003 | Morris et al. |
| 2003/0123058 | A1 | 7/2003 | Luryi et al. |
| 2003/0151741 | A1 | 8/2003 | Wolleschensky et al. |
| 2003/0153011 | A1 | 8/2003 | Bell |
| 2003/0205682 | A1 | 11/2003 | Kapoor et al. |
| 2003/0228703 | A1 * | 12/2003 | Hoppe et al. .................. 436/172 |
| 2004/0007675 | A1 | 1/2004 | Gillispie et al. |
| 2004/0207731 | A1 | 10/2004 | Bearman et al. |
| 2005/0046836 | A1 | 3/2005 | Olschewski |
| 2005/0064427 | A1 | 3/2005 | Gluch et al. |
| 2005/0112541 | A1 | 5/2005 | Durack et al. |
| 2005/0121603 | A1 | 6/2005 | Seyfried et al. |
| 2005/0123445 | A1 | 6/2005 | Blecka et al. |
| 2005/0136258 | A1 | 6/2005 | Nie et al. |
| 2005/0145497 | A1 | 7/2005 | Gilbert et al. |
| 2005/0151964 | A1 | 7/2005 | Roth |
| 2005/0179892 | A1 | 8/2005 | Gerstner et al. |
| 2005/0180634 | A1 | 8/2005 | Berman et al. |
| 2005/0227362 | A1 | 10/2005 | Lary et al. |
| 2005/0243313 | A1 | 11/2005 | Neher et al. |
| 2005/0260764 | A1 | 11/2005 | Grigsby, Jr. et al. |
| 2006/0254522 | A1 | 11/2006 | Shaw et al. |

FOREIGN PATENT DOCUMENTS

| | | |
|---|---|---|
| WO | WO 96/22575 | 7/1996 |
| WO | WO 00/06193 | 2/2000 |
| WO | WO 01/27590 A2 | 4/2001 |
| WO | WO 01/29538 | 4/2001 |

OTHER PUBLICATIONS

Keij, Jan F.; Bell-Prince, Carolyn, Steinkamp, John A., "Simultaneous Analysis of RElative DNA and Glutathione Content in Viable Cells by Phase-Resolved Flow Cytometry," Wiley-Liss, Inc., 1999, Cytometry 35, pp. 48-54.

Lansford, Rusty; Bearman, Gregory; Fraser, Scott E., "Resolution of Multiple Green Fluorescent Protein Color Variants and Dyes Using Two-Photon Microscopy and Imaging Spectroscopy," Jouranl of Biomedical Optics, vol. 6 No. 3, Jul. 2001, pp. 311-318.

Steinkamp, John A.; Habbersett, Robert C,; and Hiebert, Richard D., Improved Multilaser/Multiparameter Flow Cytometer for Analysis and Sorting of Cells and Particles, Rev. Sci. Instrum. 62(11), Nov. 1991, pp. 2751-2764.

Johnson et al., Theriogenology, vol. 52, 1999, pp. 1323-1341.

* cited by examiner

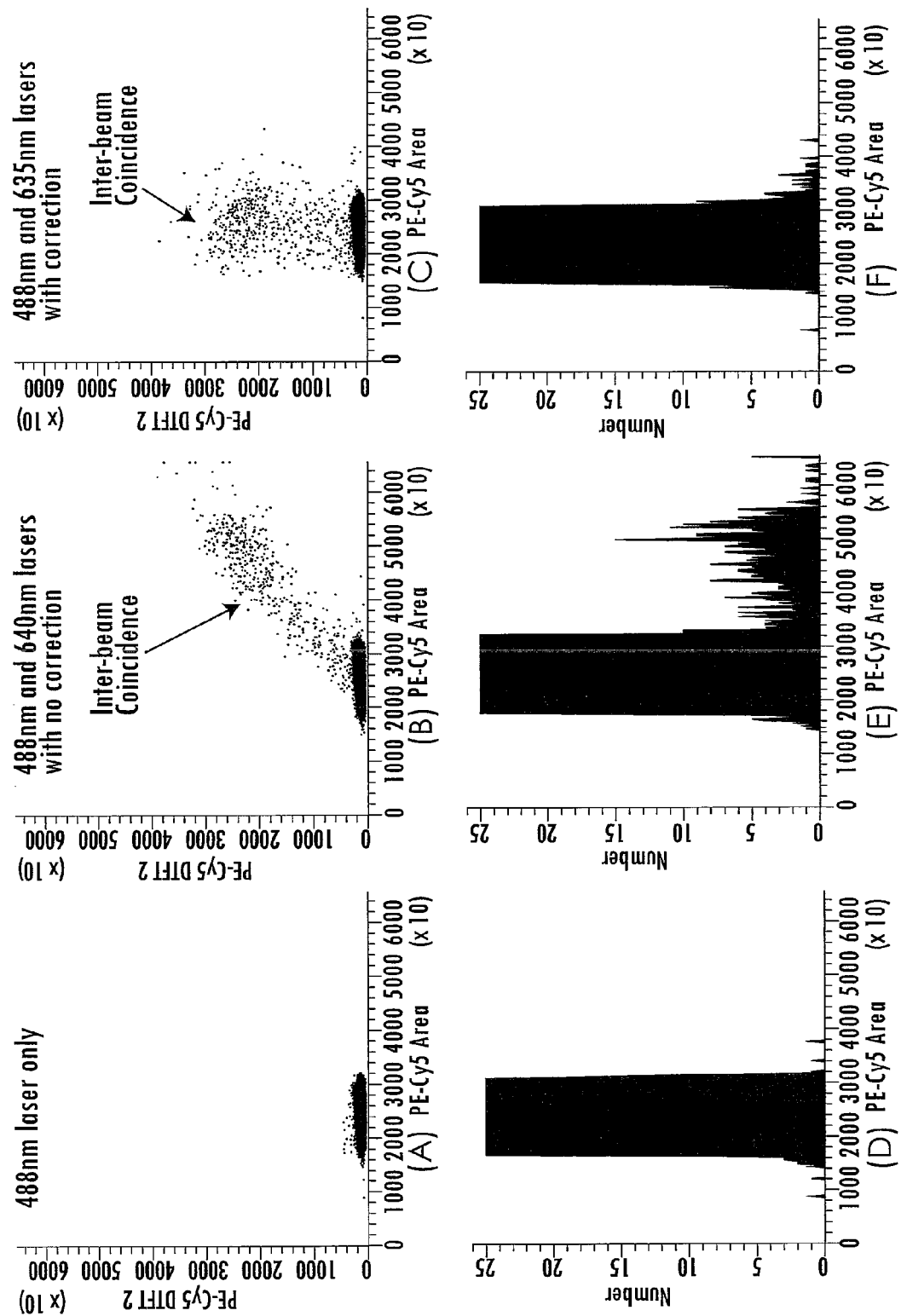

SYSTEM AND METHOD FOR THE MEASUREMENT OF MULTIPLE FLUORESCENCE EMISSIONS IN A FLOW CYTOMETRY SYSTEM

CROSS-REFERENCE TO PRIOR APPLICATIONS

The present application claims the benefit of U.S. Provisional Patent Application Ser. No. 60/892,716, filed Mar. 2, 2007 and entitled System and Method for the Measurement of Multiple Fluorescence Emissions in a Flow Cytometry System, the text and drawings of which are hereby incorporated by reference in their entireties.

TECHNICAL FIELD OF THE INVENTION

The Present invention generally relates to flow cytometry systems and, more particularly, to a system and method for the measurement of multiple fluorescence emissions in a flow cytometry system.

BACKGROUND OF THE INVENTION

Flow cytometry-based cell sorting was first introduced to the research community more than 20 years ago. It is a technology that has been widely applied in many areas of life science research, serving as a critical tool for those working in fields such as genetics, immunology, molecular biology and environmental science. Unlike bulk cell separation techniques such as immuno-panning or magnetic column separation, flow cytometry-based cell sorting instruments measure, classify and then sort individual cells or particles serially at rates of several thousand cells per second or higher. This rapid "one-by-one" processing of single cells has made flow cytometry a unique and valuable tool for extracting highly pure sub-populations of cells from otherwise heterogeneous cell suspensions.

Cells targeted for sorting are usually labeled in some manner with a fluorescent material. The fluorescent probes bound to a cell emit fluorescent light as the cell passes through a tightly focused, high intensity, light beam (typically a laser beam). A computer records emission intensities for each cell. These data are then used to classify each cell for specific sorting operations. Flow cytometry-based cell sorting has been successfully applied to hundreds of cell types, cell constituents and microorganisms, as well as many types of inorganic particles of comparable size.

There are two basic types of cell sorters in wide use today. They are the "droplet cell sorter" and the "fluid switching cell sorter." The droplet cell sorter utilizes micro-droplets as containers to transport selected cells to a collection vessel. The micro-droplets are formed by coupling ultrasonic energy to a jetting stream. Droplets containing cells selected for sorting are then electrostatically steered to the desired location. A droplet cell sorter can process selected cells at rates of tens of thousands of cells per second, limited primarily by the frequency of droplet generation and the time required for illumination.

The second type of flow cytometry-based cell sorter is the fluid switching cell sorter. Most fluid switching cell sorters utilize a piezoelectric device to drive a mechanical system which diverts a segment of the flowing sample stream into a collection vessel. Compared to droplet cell sorters, fluid switching cell sorters have a lower maximum cell sorting rate due to the cycle time of the mechanical system used to divert the sample stream. This cycle time, the time between initial sample diversion and when stable non-sorted flow is restored, is typically significantly greater than the period of a droplet generator on a droplet cell sorter. This longer cycle time limits fluid switching cell sorters to processing rates of several hundred cells per second. For the same reason, the stream segment switched by a fluid cell sorter is usually at least ten times the volume of a single micro-drop from a droplet generator. This results in a correspondingly lower concentration of cells in the fluid switching sorter's collection vessel as compared to a droplet sorter's collection vessel.

Flow cytometers are also applied widely for rapidly analyzing heterogeneous cell suspensions to identify constituent sub-populations. Fluorescently labeled monoclonal antibodies are often used as "markers" to identify immune cells such as T lymphocytes and B lymphocytes. For example, clinical laboratories routinely use this technology to count the number of "CD4 positive" T cells in HIV infected patients. They also use this technology to identify cells associated with a variety of leukemia and lymphoma cancers.

A detailed description of a prior art flow cytometry system is given in United States Published Patent Application No. US 2005/0112541 A1 to Durack et al.

Flow cytometers are often used to measure fluorescence emission intensity from single cells labeled with multiple fluorescent molecules. To obtain simultaneous labeling with the desired number of fluorescent molecules, it is often necessary to use multiple laser sources for excitation, with the excitation wavelength of each laser corresponding to that required to cause a particular fluorescent labeling molecule to fluoresce at a particular emission wavelength. In many cases, the emission spectra from fluorescent molecules excited by different lasers may overlap, causing confusion as to which fluorescent molecule is actually being detected. For example, the PE-Cy5 tandem conjugate is excited efficiently at $\lambda=532$ nm and emits at $\lambda=675$ nm, while APC is excited at $\lambda=632$ nm and also emits at $\lambda=675$ nm. When these two fluorescent dyes and lasers are used concurrently, it is necessary for the flow cytometer to employ some technique for accurately and independently quantifying the intensity of the two overlapping emissions.

This has been accomplished in the prior art by spatially separating the two focused laser beams so that each individual cell passes through the two excitation sources sequentially. Knowledge of the distance between the two excitation source focus points and the cell velocity allows the data acquisition system in the flow cytometer to correlate these temporally separated fluorescence measurements. To enable independent observation of the separate excitation laser spots, it is necessary to include a spatial filter in the emission collection optical path. This spatial filter limits the field of view of a photodetector so that most of the photons that strike it are from the emission produced by a single excitation laser spot. Typically, this spatial filter consists of a series of lenses that focus in and out of a pinhole.

The use of such spatial filtering presents many problems. Focusing through a pinhole attenuates the emission reducing the sensitivity of the system. The spatial separation between the two beams must be carefully adjusted and held constant with a high degree of accuracy. This significantly complicates optical alignment, especially in cases when more than two excitation sources are required. Very importantly, there will be times when two or more cells arrive with a close enough spacing that part or all of different cells are simultaneously in each of the two beams. Depending on the efficiency of the spatial filtering system, this can lead to varying degrees of inter-beam "crosstalk" in the detection system. Managing this "crosstalk" is a major aspect of the design of a spatial filtering system on a flow cytometers. Smaller pinholes produce greater spatial isolation, but reduce sensitivity since they attenuate the emission to a higher degree. Larger pinholes increase sensitivity, but also increase crosstalk among emission points. Furthermore, spatial separation of two beams requires that one or both of the beams be adjusted to a less than optimal position, off the axis of the fluorescence collection optic. This reduces the collection efficiency from that focus spot(s) and further compromises the sensitivity of the optical system to low level fluorescence emission. Because of this, spatial separation of the beams does not scale well with increased numbers of excitation lasers. It is not practical to use more than three separate excitation focus spots when using spatial filtering techniques. With three excitation focus spots, one can be located at the optimum focus point of the optic and the other two can be located above and below in the image plane of the optic. A fourth spot would fall out of the usable collection angle of most collection optics. Additionally, spatial filtering requires that two detectors be used to collect the emission for the same wavelength band. This introduces significant additional expense as the photodetector and all optical components in the optical train (lenses, optical filters, etc.), plus all detection path electronic components (amplifiers, analog-to-digital converters, etc.) must be duplicated.

There is therefore a need in the prior art for a system and method of collecting fluorescent emission intensity in a flow cytometer system having multiple excitation sources. The present invention is directed to meeting this need.

SUMMARY OF THE INVENTION

In one embodiment, a flow cytometer for measuring fluorescent emission from a particle is disclosed, the flow cytometer comprising a first excitation light source producing a first modulated excitation beam modulated at a first frequency; a second excitation light source producing a second modulated excitation beam modulated at a second frequency, said second frequency being different than said first frequency; beam combining optics adapted to receive said first and second modulated excitation beams and produce a combined modulated excitation beam; a detector adapted to measure fluorescent emission from said particle when said particle is within said combined modulated excitation beam, said detector producing a detector output signal; and a signal processor operatively coupled to said detector for receipt of said detector output signal, said signal processor operative to distinguish a first portion of said detector output signal caused by excitation of said particle by said first modulated excitation beam and a second portion of said detector output signal caused by excitation of said particle by said second modulated excitation beam.

In another embodiment, a method for measuring fluorescence emissions from a particle in a flow cytometer is disclosed, comprising the steps of (a) providing a first excitation light source; (b) modulating said first excitation light source at a first frequency to produce a first modulated excitation beam; (c) providing a second excitation light source; (d) modulating said second excitation light source at a second frequency to produce a second modulated excitation beam, said second frequency being different than said first frequency; (e) combining said first and second modulated excitation beams to produce a combined modulated excitation beam; (f) shining said combined modulated excitation beam on a particle; (g) detecting fluorescent emission from said particle; and (h) determining a first portion of said detected fluorescent emission caused by excitation of said particle by said first modulated excitation beam and a second portion of said detected fluorescent emission caused by excitation of said particle by said second modulated excitation beam.

In another embodiment, a flow cytometer for measuring fluorescent emission from a particle, the flow cytometer comprising a first excitation light source producing a first modulated excitation beam modulated at a first frequency; a second excitation light source producing a second modulated excitation beam modulated at a second frequency, said second frequency being different than said first frequency; first optics adapted to focus said first modulated excitation beam at a first focus spot; second optics adapted to focus said second modulated excitation beam at a second focus spot, said second focus spot being spatially separated from said first focus spot; a detector adapted to measure fluorescent emission from said particle when said particle is within either said first focus spot or said second focus spot, said detector producing a detector output signal; and a signal processor operatively coupled to said detector for receipt of said detector output signal, said signal processor operative to distinguish a first portion of said detector output signal caused by excitation of said particle by said first modulated excitation beam and a second portion of said detector output signal caused by excitation of said particle by said second modulated excitation beam.

In another embodiment, a method for measuring fluorescence emissions from a particle in a flow cytometer is disclosed, comprising the steps of (a) providing a first excitation light source; (b) modulating said first excitation light source at a first frequency to produce a first modulated excitation beam; (c) providing a second excitation light source; (d) modulating said second excitation light source at a second frequency to produce a second modulated excitation beam, said second frequency being different than said first frequency; (e) focusing said first modulated excitation beam to a first focus spot; (f) focusing said second modulated excitation beam to a second focus spot; (g) causing a particle to traverse said first and second focus spots; (h) detecting with a single detector fluorescent emission from said particle when said particle is within either said first focus spot or said second focus spot; (i) determining a first portion of said detected fluorescent emission caused by excitation of said particle by said first modulated excitation beam and a second portion of said detected fluorescent emission caused by excitation of said particle by said second modulated excitation beam.

In another embodiment, a flow cytometer for measuring fluorescent emission from a particle is disclosed, the flow cytometer comprising a first excitation light source producing a first modulated excitation beam modulated at a first frequency; a second excitation light source producing a second modulated excitation beam modulated at a second frequency, said second frequency being different than said first frequency; first optics adapted to focus said first modulated excitation beam at a first focus spot; second optics adapted to focus said second modulated excitation beam at a second focus spot, said second focus spot being spatially separated from said first focus spot; a detector adapted to measure fluorescent emission from said particle when said particle is within either said first focus spot or said second focus spot, said detector producing a detector output signal; and a signal processor operatively coupled to said detector for receipt of said detector output signal, said signal processor operative to distinguish a first portion of said detector output signal caused by excitation of said particle by said first modulated excitation beam and a second portion of said detector output signal caused by excitation of said particle by said second modulated excitation beam, said signal processor further operable to correct said detector output signal for the effects of inter-beam coincidence.

In another form of the invention, a method for measuring fluorescence emissions from a particle in a flow cytometer is disclosed, comprising the steps of (a) providing a first excitation light source; (b) modulating said first excitation light source at a first frequency to produce a first modulated excitation beam; (c) providing a second excitation light source; (d) modulating said second excitation light source at a second frequency to produce a second modulated excitation beam, said second frequency being different than said first frequency; (e) focusing said first modulated excitation beam to a first focus spot; (f) focusing said second modulated excitation beam to a second focus spot; (g) causing a particle to traverse said first and second focus spots; (h) detecting with a single detector fluorescent emission from said particle when said particle is within either said first focus spot or said second focus spot; (i) determining a first portion of said detected fluorescent emission caused by excitation of said particle by said first modulated excitation beam and a second portion of said detected fluorescent emission caused by excitation of said particle by said second modulated excitation beam; and (j) correcting said detector output signal for the effects of inter-beam coincidence.

BRIEF DESCRIPTION OF THE DRAWINGS

FIGS. 14A-F illustrate how traditional pulse area measurements are corrected using the embodiments disclosed herein and how the constants C1 and C2 are determined empirically.

DETAILED DESCRIPTION OF THE VARIOUS EMBODIMENTS

Figure 1:
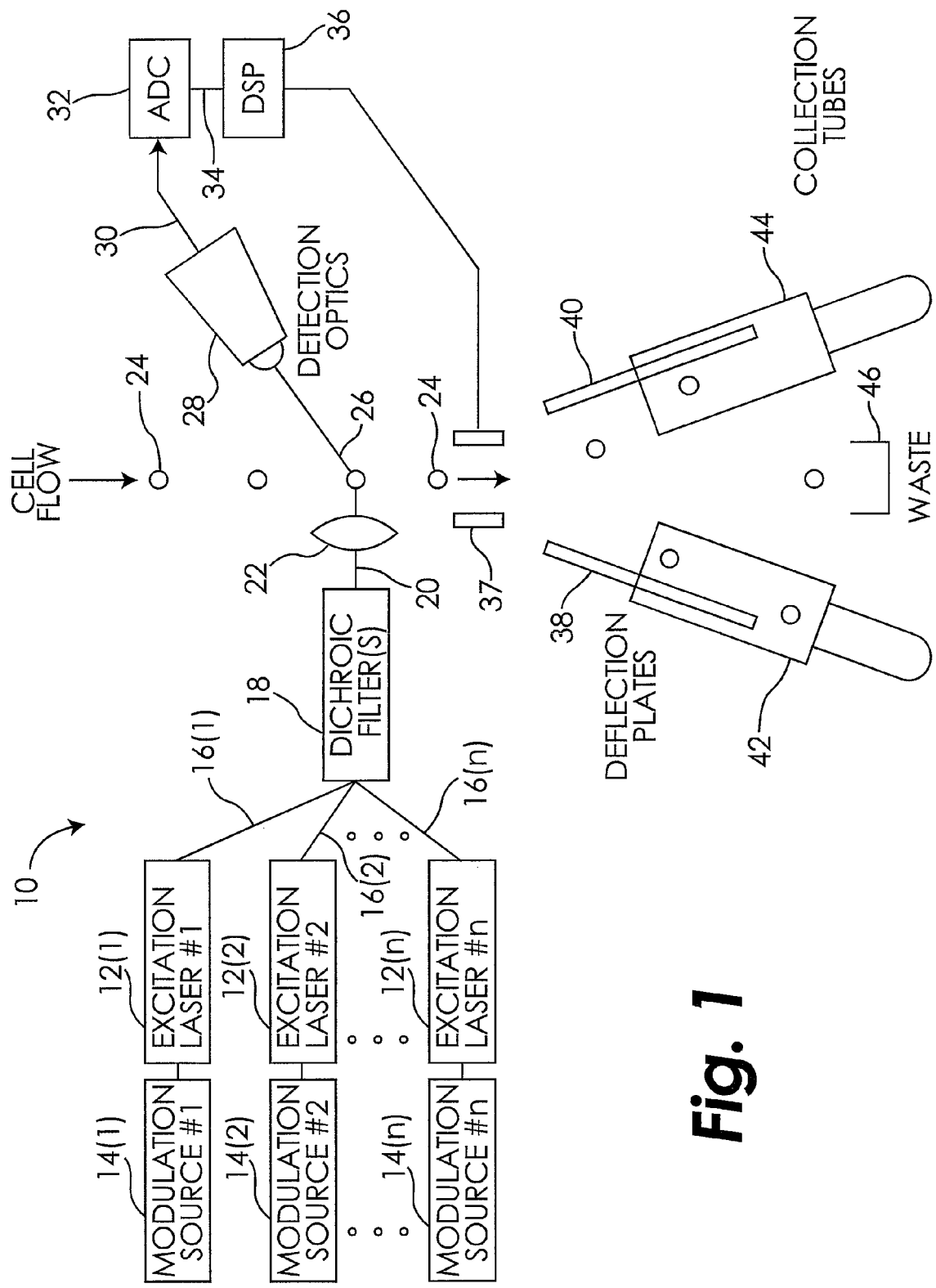
FIG. 1 is schematic block diagram of a first embodiment flow cytometry system.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates are intended to be protected.

The present embodiments disclosed herein comprise a scaleable approach to measuring overlapping spectral emission originating from multiple fluorescence excitation sources in a flow cytometry system. With reference to FIG. 1, a first embodiment flow cytometry system is indicated generally at 10. The flow cytometry system 10 includes multiple excitation light sources 12(1) through 12(n), where n is an integer greater than one. Excitation light sources 12 may comprise, for example, laser light sources to name just one non-limiting example. Each of the excitation lasers 12 are amplitude modulated in one embodiment with an appropriate function (such as a sinusoid function ($\sin$ or $\sin^2$) to name just one non-limiting example) at specific known frequencies.

Many diode lasers can be directly amplitude modulated using transistor-transistor logic (TTL) gating (one example of such a laser is the CUBE™ laser series from Coherent, Inc., 5100 Patrick Henry Drive, Santa Clara, Calif. 95054) or by introducing a periodic signal (sine wave, square wave) into the electronics driving the diode laser. Many lasers produce highly periodic pulse trains due to their physical cavity design. An example of such a laser is the VANGUARD™ 350-HMD 355 laser (available from Newport Corporation, 1791 Deere Avenue, Irvine Calif. 92606) which produces pulses at a frequency of approximately 80 MHz. Lower modulation frequencies can be achieved by using an electro-optic modulator (EOM) or an acousto-optic modulator (AOM). EOMs and AOMs are used to introduce amplitude, phase, or frequency modulation onto continuous-wave (CW) laser beams. It will be appreciated that the various embodiments disclosed herein can be used with amplitude, phase or frequency modulation, or a combination of these techniques. Any method of producing periodic excitation in the light source will produce periodic fluorescence emission from the fluorescent tag that can be analyzed using the systems and methods described herein.

The present embodiment of the invention is for use in a high speed cell sorting application. As used herein, the words "cell" and "particle" are interchangeable. Although "cell" refers to a biological material and "particle" refers to non-biological material, the systems and methods disclosed herein work with either cells or particles, therefore the words are interchangeable in the present disclosure and claims. In the case of high speed cell sorting, cells flow past the optical system at velocities of 10-50 m/s (depending on the fluid pressure employed). This produces dwell times in the optical measurement region of <2 microseconds. Both higher and lower velocity systems can also be employed that could result in dwell times of 10 nanoseconds to 500 milliseconds. Because it is desirable to have >2 periods of the modulation occur during the dwell time, modulation frequencies may preferably be between about 10 KHz and 1 GHz. For the high speed cell sorter embodiment of the invention, the modulation frequencies are more preferably between 5 MHz and 40 MHz.

Figure 2:
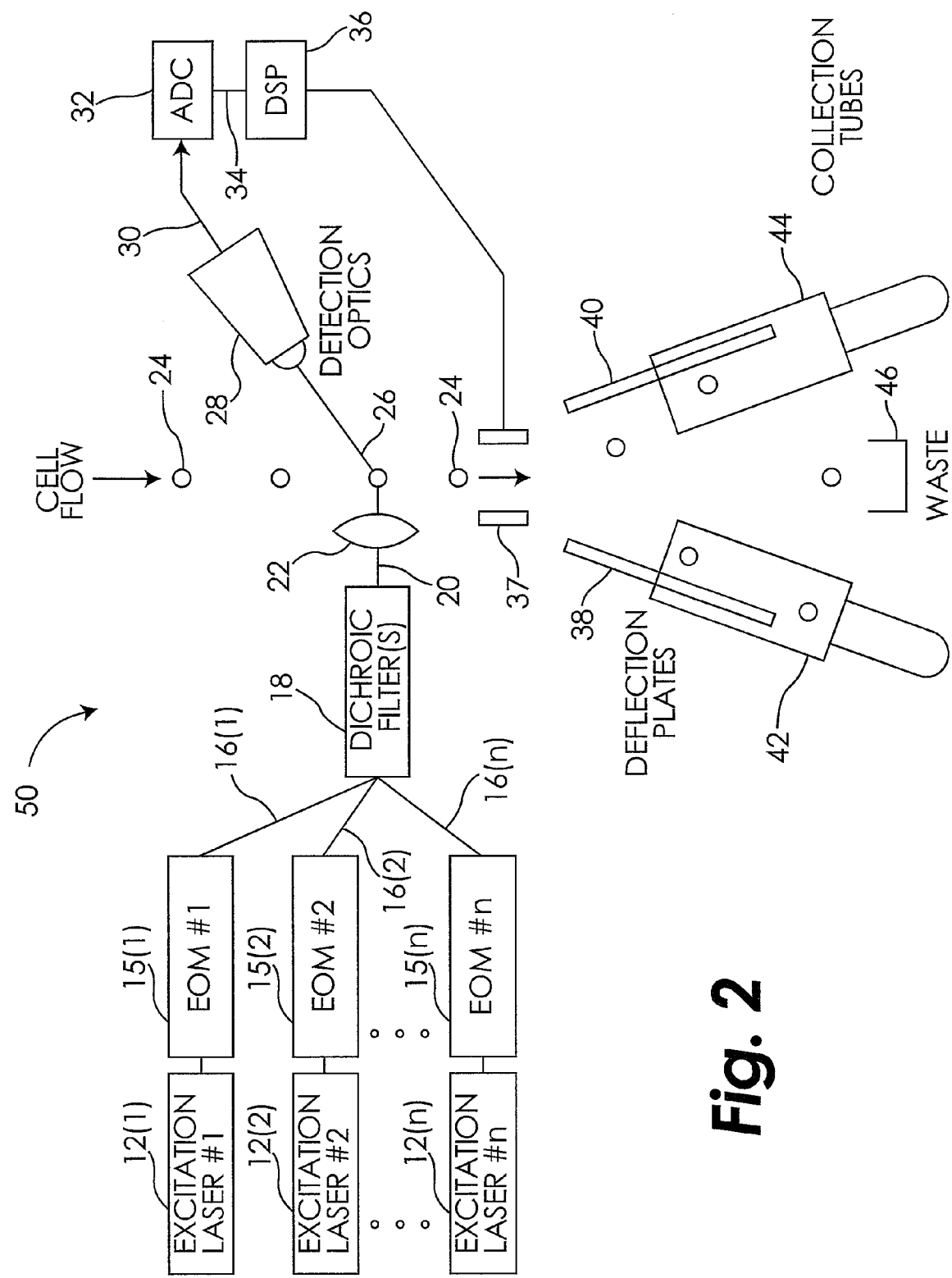
FIG. 2 is schematic block diagram of a second embodiment flow cytometry system.

In one embodiment, such modulation is accomplished using modulated power sources 14(1) through 14(n) that are used to drive the excitation lasers 12(1) through 12(n). In another embodiment, an electro-optic modulator (EOM) may be used to modulate the light emitted from each excitation laser. An electro-optic modulator is an optical device in which a signal-controlled element is used to modulate a beam of light. It is based on the linear electro-optic effect (also called Pockels effect), i.e., the modification of the refractive index of a nonlinear crystal by an electric field in proportion to the field strength. The modulation may be imposed on the phase, frequency, amplitude, or direction of the modulated beam. Modulation bandwidths extending into the gigahertz range are possible with the use of appropriate modulators. When using EOMs, the EOMs 15(1) through 15(n) are placed to receive the output of each respective excitation laser 12, as is shown in the second embodiment flow cytometry system 50 of FIG. 2. In either arrangement, each excitation light source 12 is modulated at a different frequency and/or in a different manner.

The individual modulated excitation laser beams 16(1) through 16(n) are combined into a single, collinear, combined excitation beam 20 by the use of dichroic filters 18 or other suitable optics, as is known in the art. This combined excitation beam is focused (using optics 22) such that the waists of each of the individual lasers overlap at a single point (the detection volume), through which cells 24 in the flow cytometer pass. For example, the cells may flow through the focus spot of the combined excitation beam while they are within the flow of liquid (not shown) and before droplet (not shown) formation. Interaction of the combined excitation beam 20 with a cell 24 may result in a fluorescence emission 26. Detection optics 28 focuses the fluorescence emission 26 onto a photodetector (not shown), such as a photomultiplier tube (PMT) operating in analog mode (not photon counting). In front of the PMT are preferably located optical filters that discriminate a particular spectral band of interest (i.e. the expected band of fluorescence emitted by the labeling fluorescent molecules). In some embodiments, a single set of optics will transmit the emission to multiple PMTs, each having an associated bandpass filter that allows one range of expected emission frequencies to pass to the PMT. For example, the emission can be coupled into a fiber optic system and then input into multiple PMTs. Optical filters, including narrow-band notch filters, may be employed to block intense laser light scatter from the stream or particles.

In one embodiment, the PMT and associated amplification system have a bandwidth of approximately 45 MHz (0.5-45 MHz). This bandwidth is selected such that it includes all of the modulation frequencies employed, however the highest passed frequency is preferably less than 2.5 times the digital sampling frequency used for data acquisition. The Nyquist theorem states that to prevent harmonic artifacts in digital sampled data, the frequency content of the signal must be limited to less than two times the sampling frequency. The analog signal 30 out of the detection optics 28 is continuously sampled at a rate greater than the Nyquist frequency by analog-to-digital converter (ADC) 32 to produce a digitized version 34 of the detected analog signal 30. In one embodiment, the ADC 32 utilizes a sample rate of 105 MHz using a 14 bit ADC. In some embodiments where multiple PMTs are used, a separate ADC is preferably used to sample the analog output of each PMT. The digitized data stream 34 is analyzed in a suitable data processor, such as digital signal processing system (DSP) 36 using appropriate software.

This software detects and analyzes the digitized waveform produced by the electrical pulse from the PMT which resulted from fluorescence emission of the fluorescent molecules in the cell 24. The fluorescence emission was produced by the fluorescently labeled cells 24 passing through the combined (simultaneous) laser excitation 20. Sinusoidal excitation of fluorescent molecules produces a nearly sinusoidal fluorescence emission intensity from those molecules. The phase shift of the modulated emission and the modulation depth of the modulated emission are related to the lifetime of the emission decay. The frequency of the modulated emission will match the frequency of the excitation source. The combined fluorescence emission of the cell 24 detected by detection optics 28, therefore, can be represented as a sum of sinusoidal functions, one frequency for each individual excitation laser 12 which caused a fluorescent emission from the cell 24.

By computing Discrete Time Fourier transforms (DTFTs) at the known modulation frequencies of the excitation laser beams 16 on the digital data 34 obtained by sampling the electrical signal 30 from the PMT, the DSP 36 determines the power present in the signal at each modulation frequency. This power is proportional to the emissions of the fluorescent material due to excitation by individual light source 12 which is modulated at that frequency. The DTFT computations may be used to unmix the emission signal 26 into its component parts, one for each laser 12, even if these emissions have overlapping spectral characteristics, and to derive the intensity of each separate emission component. The DSP may also, in some embodiments, compute the total fluorescence emission from the cell 24 by computing the total area of the emission pulse.

Upon determining these separate emission intensities for any particular cell 24, the DSP 36 may use this information to determine how to classify and electrostatically sort the droplet containing the cell, as is known in the art. It should be noted that the system may also be used to analyze the samples but not sort them. In other words, the system may count populations within the entire sample, but not sort those populations into separate physical collections. In one embodiment involving sorting of the cells 24, the DSP 36 may control an electrical charging system 37 that is used to induce a charge onto the droplet containing the cell 24. Deflection plates 38 and 40 are each coupled to fixed potentials in order to deflect the cell 24 in different directions depending upon what charge is placed upon the droplet containing the cell 24 by the system 37. The deflection plates 38 and 40 will sort the cell 24 into the appropriate collection tubes 42 or 44, or allow the cell 24 to enter the waste receptacle 46, as is known in the art. For the high speed flow cytometry cell sorter, cells arrive at random intervals at average rates of up to 100,000 cells per second or more. By using the multi-emission measurement described herein, classification and the sorting decision must be accomplished within a few hundred microseconds. The computations must be performed in real-time in order to sort the cells into the appropriate collection vessels. The use of the DTFT algorithm and the high-speed processing architecture disclosed herein are essential to achieving a practical solution for cell sorting at these rates.

Figure 3:
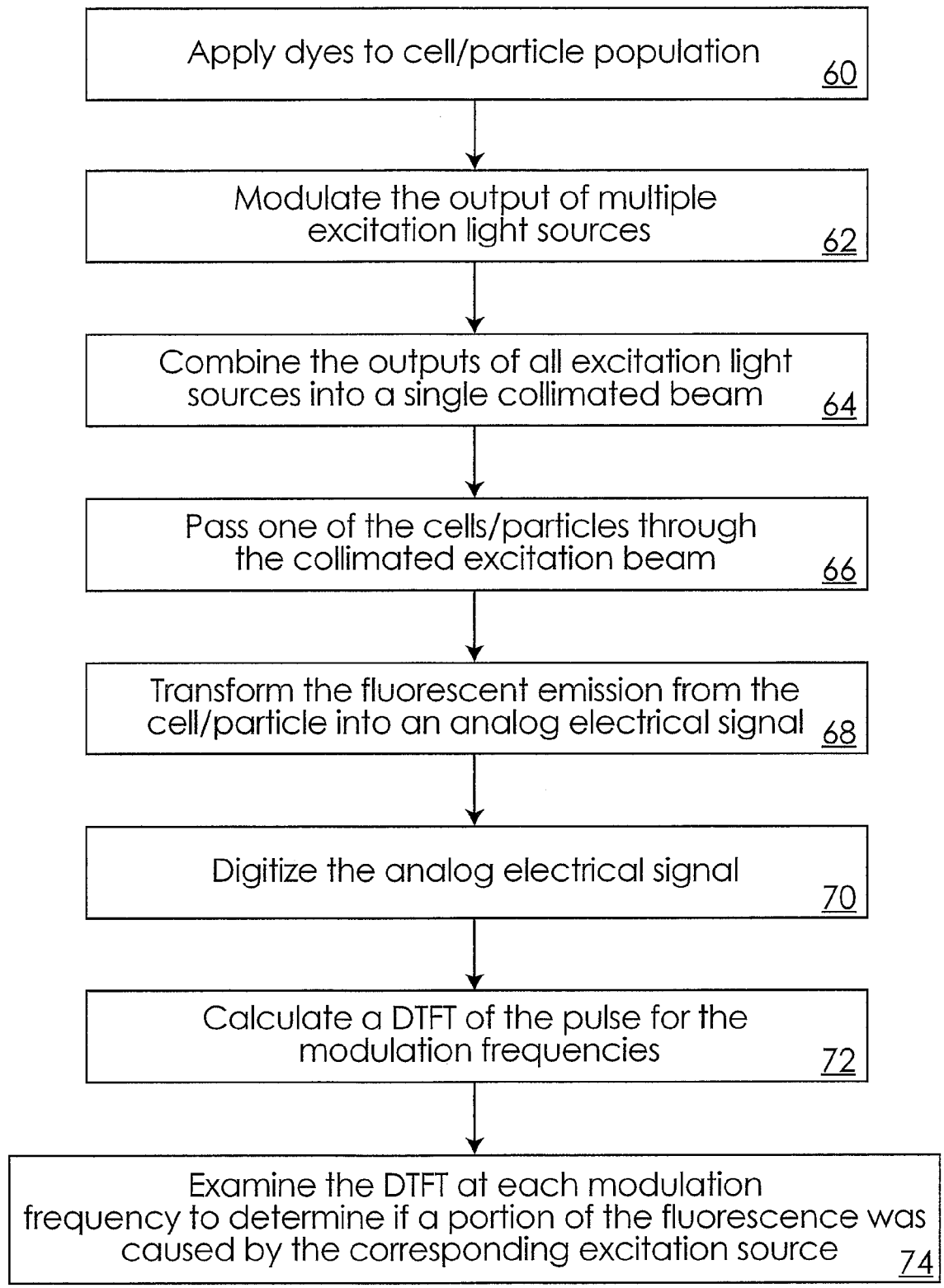
FIG. 3 is a schematic process flow diagram of a first embodiment method for measuring multiple fluorescent emissions in a flow cytometry system.

A schematic process flow diagram for detection of multiple fluorescent emissions using the systems 10 and 50 is illustrated in FIG. 3. The process begins at step 60 where multiple dyes are applied to the population of cells or other particles. Each particular dye used will have an excitation, or absorption spectra and a resultant fluorescence emission spectra. Fluorescent emission will always occur at longer wavelengths due to the physical property of fluorescence known as Stoke's shift. Some or all of the emission wavelengths from the various dyes may overlap. The dyes can be excited by one or more of the excitation sources.

At step 62, an excitation light source having an excitation wavelength corresponding to the excitation spectra of at least one of the dyes is modulated in a manner different than the other excitation light sources. For example, each excitation light source may be amplitude modulated with a sine function having a different frequency than all of the other modulation frequencies.

At step 64, the modulated outputs of all of the excitation light sources are combined into a single excitation light beam. One of the cells/particles from the population under study is passed through the focus of the excitation beam at step 66, causing fluorescent emissions corresponding to each dye present on the cell/particle.

This fluorescent emission is transformed at step 68 by the detection optics of the system, producing an analog electrical signal corresponding to the time-varying intensity of the emission pulse. This analog signal is digitized at step 70 so that the data can be analyzed with use of digital signal processing equipment. A DTFT is performed on this digitized pulse signal at step 72 for at least the modulation frequencies of the individual excitation light sources. The value of the DTFT, calculated at each of these modulation frequencies, corresponds to the portion of the total output signal contributed by emissions resulting from each of the individual excitation light sources. These DTFT values are then examined at step 74 to determine the contribution of each excitation source to the total fluorescence emission. By determining whether the DTFT values at each modulation frequency fall within predetermined ranges, the system can determine whether the cell/particle that just passed through the focused beam is marked with specific amounts of the corresponding dyes, and appropriate action can be taken to sort the cell/particle.

The flow cytometry systems 10 and 50 can be used with any number of excitation light sources 12. It will be appreciated from the above description that the flow cytometry system 10 represents a significant improvement over prior art multiple excitation source systems. First, no spatial separation between the excitation light source beams needs to be adjusted and held constant with a high degree of accuracy, thus simplifying the set up and operation of the flow cytometry system 10. Also, the possibility of crosstalk between the multiple beams is eliminated, as the optical system need not isolate emission photons produced by multiple excitation sources. Additionally, for any specific wavelength band, only one detector 28 is needed no matter how many excitation light sources 12 are used. Simultaneous, quantitative, fluorescence measurements from each excitation source can be made using the same optical elements and photodetector, removing variability introduced by prior multi-optical path, multi-detector implementations. Furthermore, since only a single, combined excitation beam 20 is used, the system 10 does not require any off axis collection optics which can compromise the sensitivity of the optical system to low level fluorescence emission. Finally, the system 10 scales well to large numbers of lasers 12, since they are all combined in a collinear fashion into a single beam 20 and only a single detector 28 is used for a given wavelength band. It will be appreciated that all of these improvements offer significant performance advantages over the prior art flow cytometry systems.

EXAMPLE 1

Electro-optic modulators (EOMs) (manufactured by Nova Phase, Inc., 43 Sparta Avenue, Newton, N.J. 07860) were used to modulate the continuous wave (CW) outputs of a LYT 200™ laser ($\lambda$=488 nm, power=100 mW, available from iCyt Visionary Bioscience, P.O. Box 1593, Champaign, Ill. 61824-1593) and an INNOVA® 90-C laser ($\lambda$=514 nm, power=100 mW, available from Coherent, Inc., 5100 Patrick Henry Drive, Santa Clara, Calif. 95054). The 488 nm laser was amplitude modulated using a sine function at 20 MHz and the 514 nm laser was amplitude modulated at 34 MHz. Ten micron diameter latex particles, labeled with a broad emission fluorescent dye that is stimulated into fluorescence at both 488 nm and 514 nm, were run through an iCyt Visionary Bioscience prototype cell sorter. Data were collected using custom software running on a Bittware TigerSharc DSP board equipped with a 105 MHZ Barracuda ADC (both available from Bittware Incorporated, 9 Hills Avenue, 2nd Floor, Concord, N.H. 03301). Data were collected using each laser independently in CW and modulated modes.

Figure 4:
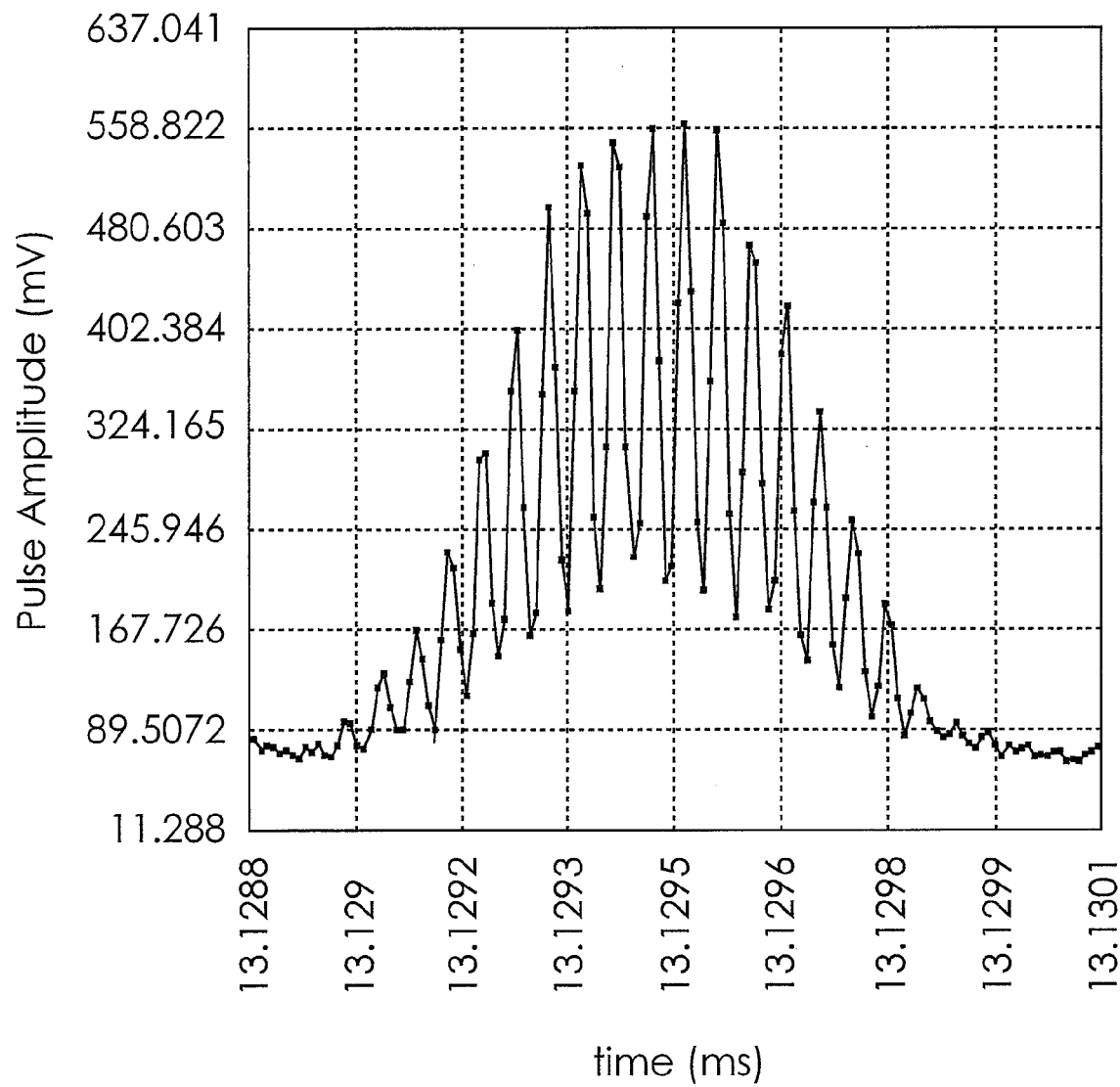
FIG. 4 is a graph of pulse amplitude vs. time of a single pulse from a flow cytometry detector, produced by a single particle passing though the focused excitation, where the excitation laser was a 514 nm laser, modulated at 34 MHz.
Figure 5:
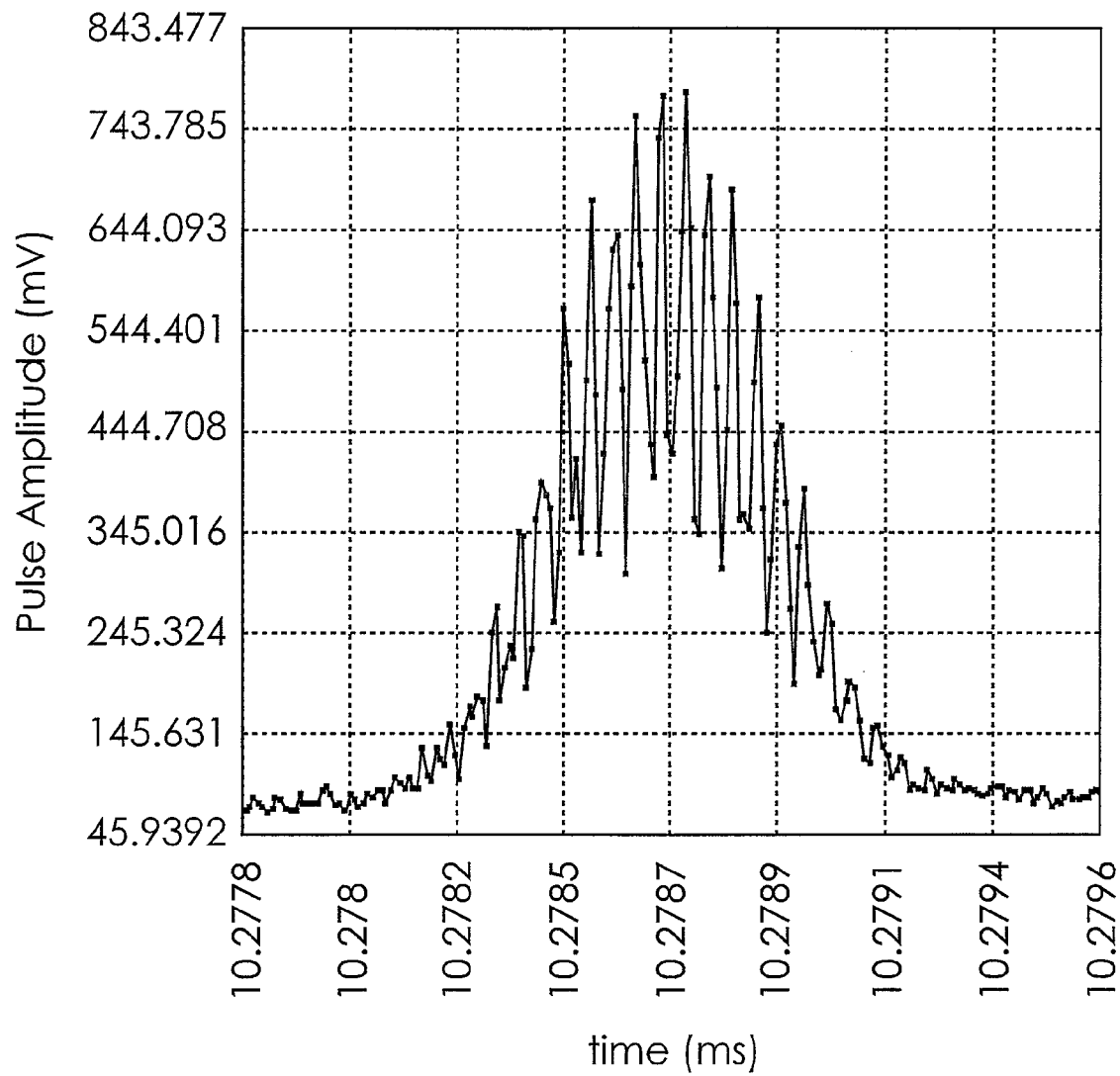
FIG. 5 is a graph of pulse amplitude vs. time of a single pulse from a flow cytometry detector, produced by a single particle passing though the focused excitation, where two excitation lasers (a 514 nm laser, modulated at 34 MHz, and a 488 nm laser, modulated at 20 MHz) were used.
Figure 6:
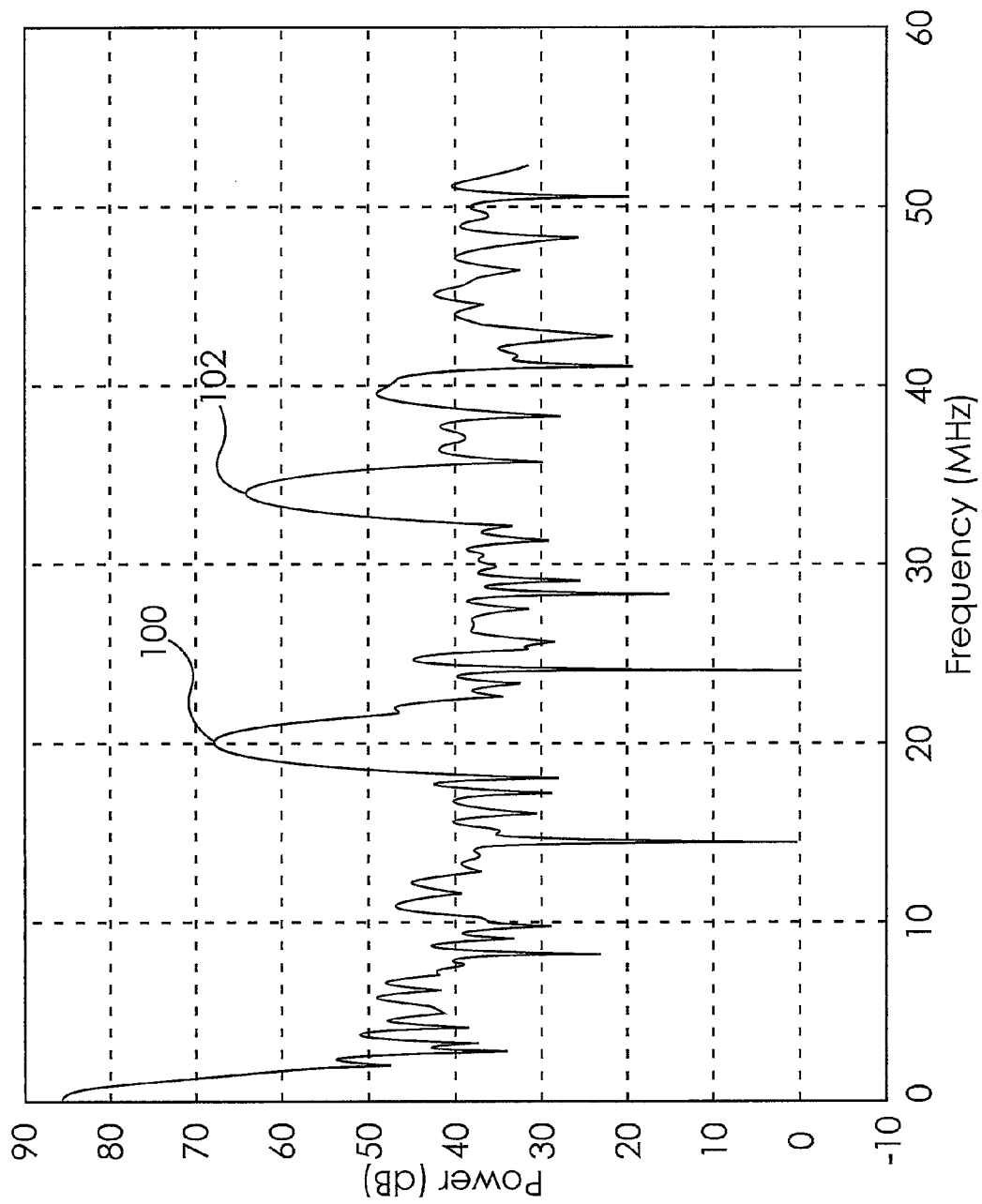
FIG. 6 is a graph of power vs. frequency calculated from the data of FIG. 5 using a Discrete Fourier Transform for frequencies up to 52.5 MHz.

The temporal signal for a single pulse from the PMT detector, resulting from the passage of a single particle through the laser beam(s) focus spot is shown in FIG. 4, where the modulation of the fluorescence was measured when only the 514 nm laser, modulated at 34 MHz, was used. FIG. 5 shows the temporal signal for a single pulse from the PMT detector, where the modulation of the fluorescence was measured when both the 488 nm laser, modulated at 20 MHz, and the 514 nm laser, modulated at 34 MHz, were simultaneously used and focused to the same point. In FIGS. 4 and 5, the data point dots indicate the time each sample was taken by the ADC. The software was used to detect pulses in the data and then perform a Fourier analysis on the segregated pulse data. Since this experiment was performed "off-line" (i.e. the data from the PMT detector was captured and then later analyzed) and thus no real-time processing constraint existed, the Power Spectral Density (PSD) of the signal was calculated for frequencies up to 52.5 MHz. FIG. 6 shows the PSD of the signal across this frequency range.

It will be appreciated that the PSD data of FIG. 6 shows two clearly defined peaks, a peak 100 located at 20 MHz and a second peak 102 located at 34 MHz. The peaks 100 and 102 correspond to the two modulation frequencies of the excitation lasers. The maximum, or peak value, at each of these frequencies correlates with the magnitude of the fluorescence emission caused by the respective excitation laser modulated at that frequency. Using this information it is possible to clearly discriminate and quantitatively measure the components of the total fluorescence emission attributable to each excitation laser, even in a sample where there is nearly 100% overlap in the spectra of the fluorescence generated. Data analysis indicates that the total fluorescence measurement produced by this method using modulated excitation lasers (for each laser independently and with both lasers present) correlates very well with the total fluorescence measured when each laser is used independently in CW mode (the traditional method).

Dynamic Range of the Detector

In some cases, there can be two potential problems associated with the previously described modulation technique. First, when all of the excitation lasers are collinear, fluorescent emission from the sample occurs simultaneously when multiple excitation lasers are used. Since, in practice, the photodetector has a limited measurement range (i.e. dynamic range of response), the amount of dynamic range available for measurement of the emission excited by each laser is not always constant, and is always less than for the case of separate beam spots. Additionally, in some cases, the minimum detection point of the fluorescence emission at any frequency that can be achieved through the use of modulation-based measurement techniques is may be higher (poorer) than the minimum detection point that can be achieved by direct measurement of the total fluorescence emission (typical area flow cytometry parameter) when different excitation lasers do not have to be discriminated.

For applications where the above problems would affect the efficacy of the measurement, the present inventors have developed a technique that combines the advantages of separately focused laser beams with the advantages of modulation-based fluorescence unmixing described hereinabove. This technique is described herein below.

Figure 7:
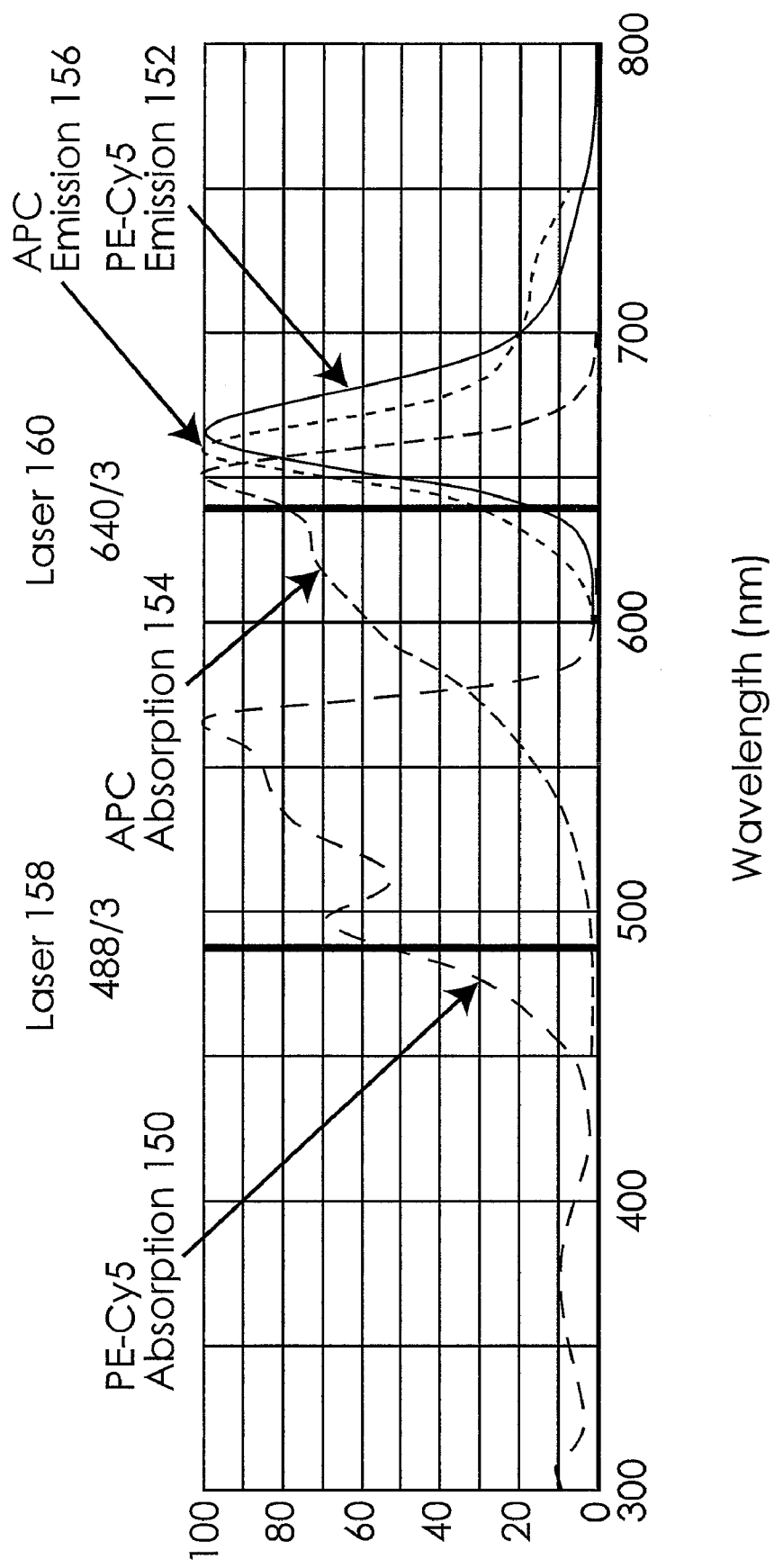
FIG. 7 is a graph illustrating overlapping spectral emissions from two fluorescent markers excited at different excitation wavelengths.

As previously discussed, a single particle or cell can be labeled with fluorescent molecules that have different excitation spectra, but may have overlapping emission spectra. An example of such labeling is illustrated in FIG. 7, where the excitation and emission spectra for two commonly used fluorescent probes that exhibit these characteristics are illustrated. Shown in FIG. 7 are the absorption spectrum 150 and the emission spectrum 152 for R-phycoerythrin-cyanin 5 tandem conjugate (PE-Cy5). Also shown are the absorption spectrum 154 and the emission spectrum 156 for allophycocyanin (APC). PE-Cy5 is commonly excited using a 488 nm laser 158 as indicated. APC is commonly excited using a 640 nm laser 160 as indicated. The emission spectra 152 and 156 of both probes overlap, and both emission spectra are centered near 675 nm.

In the present embodiment, excitation lasers, whose excitation of a sample can produce overlapping spectral emission such that the bandpass filters on the detector instrument cannot adequately discriminate them, are focused to spatially separated spots. These spots are aligned vertically on the micro-droplet jetting stream (or in a cuvette). The separation among the laser focus spots is designed to be such that when a properly labeled particle passes through the spots, a single photodetector positioned to receive fluorescence emissions from all such spatially separated spots will produce a series of temporally displaced output pulses. The distance between the successive laser focus spots (i.e. the degree of temporal separation) is designed such that the detector output pulse will fall back to baseline between transit of successive laser focus spots by the particle. This means that the spatial separation is greater than the sum of the respective beam radii plus 1 diameter of the particle ($r_{laser1}+r_{laser2}$+particle diameter).

The data acquisition system is triggered when one or more designated photodetector(s) identify a pulse (usually light scatter, but it can be fluorescence) at only one of the laser focus spots. The data acquisition system is programmed, through the use of a sample consisting of particles labeled with dyes that provide very broad absorption and emission spectra, with the temporal separation among the laser focus spots. It uses this known temporal offset and the pulse duration (number of ADC samples) as determined by the "trigger" channel to collect and analyze successive blocks of ADC samples with the transit of the particle through each successive laser.

Figure 8:
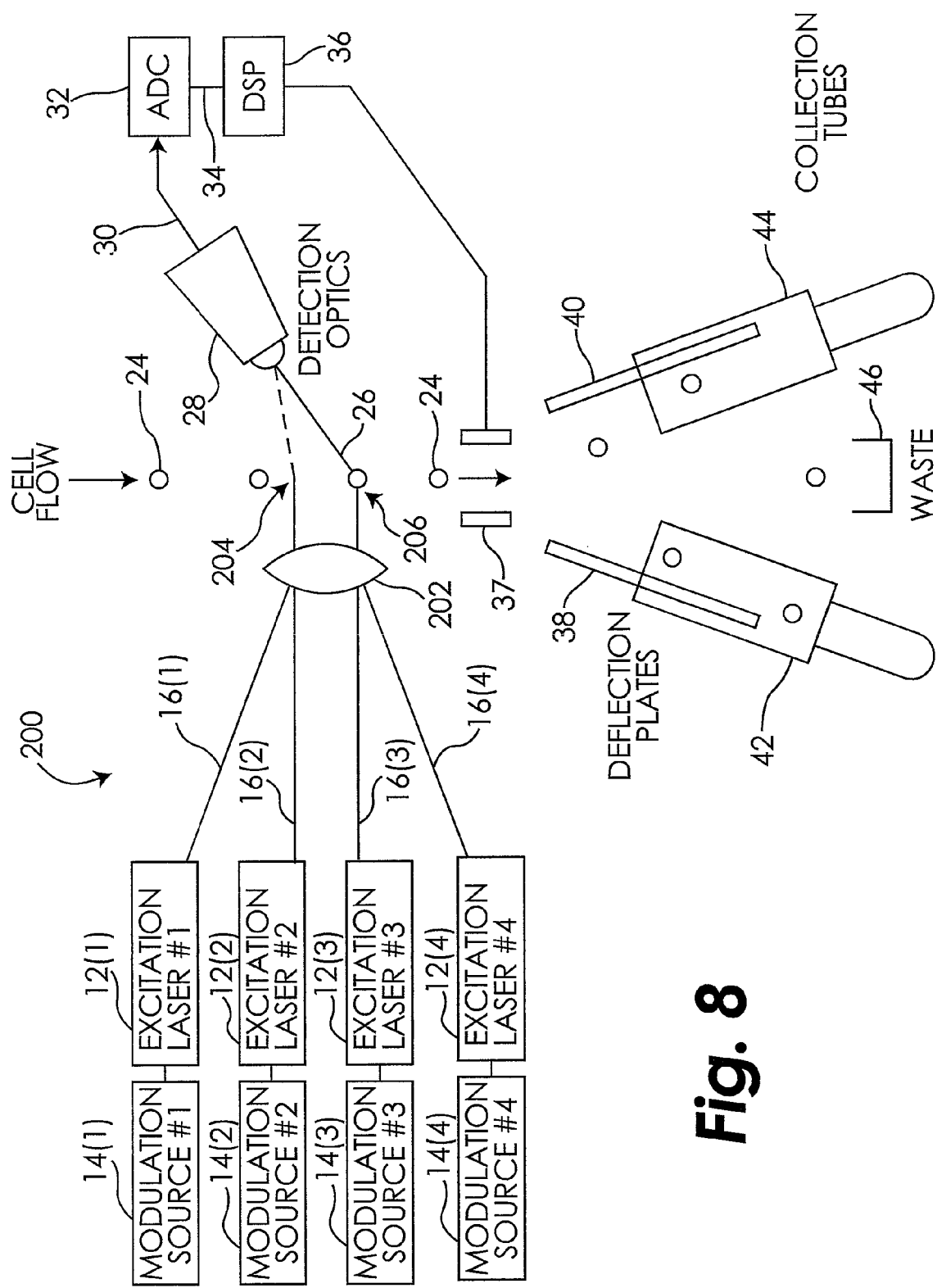
FIG. 8 is a schematic block diagram of a third embodiment flow cytometry system.

This embodiment is schematically illustrated in FIG. 8, and indicated generally at 200. The system 200 employs multiple excitation light sources modulated to different frequencies as disclosed hereinabove with respect to FIGS. 1 and 2. In the schematic illustration of FIG. 8, four such lasers 12(1) through 12(4) are used. The modulated light output 16(1) through 16(4) of the lasers is aimed at focusing optic 202. In one embodiment, optic 202 comprises a single achromatic doublet that has a focal length of 50 mm. Since separate focus spots are desired for this embodiment, the individual excitation beams enter the optic vertically offset from one another (i.e. they are aligned in the plane of the cell stream). Using this technique, we can focus lasers 12(1) and 12(2) to a single focus spot (waist) 204 and we can focus lasers 12(3) and 12(4) to a second single focus spot 206. In this embodiment, the spot sizes are about 20 microns, separated by 10-microns. The detection optic 28 is positioned so as to receive fluorescent emission from a cell 24 passing through either focus spot 204 or 206.

As will be appreciated, by focusing the lasers to spatially separated spots, the full bandwidth and amplitude dynamic range of the photodetector is available for measurement of any fluorescent emission from the particle. In order to fully analyze any individual particle, the signal processing system will examine the collection of digital samples that were obtained from the sequential analog pulses that are representative of the particle passing through each of the spatially separated laser focus spots. The digital signal processor is used to calculate a variety of features that are descriptive of the pulse. Among these features are the peak height, area, pulse width, and pulse rise time. The digital signal processor also is used to calculate a DTFT at the modulation frequency for each of the lasers in use, as described hereinabove. In this way, the system is still able to use the excitation source modulation frequencies to differentiate what portion of the total fluorescent emission from the particle is attributable to each of the excitation light sources.

This is particularly important when two or more cells are present simultaneously in the multiple focus spots. When this inter-beam coincidence occurs, it is possible for emission from two focus spots to occur simultaneously. The calculated DTFT values can be used by the digital processing system to correct for any contribution to the recorded emission pulse that originated from a focus spot other than the intended measurement focus spot, as described below.

The above described spatial separation method of measurement will work fine as long as two particles with overlapping spectral emission characteristics are never in two (or more) of the excitation beams at the same time. Since the inter-particle spacing is random, this is an unrealistic expectation. The previously described fluorescence unmixing technique embodying the use of modulated lasers is applied to address such cases. In this embodiment, however, the computed DTFT values are used to detect and/or to correct for "contaminating spectral overlap" caused by the simultaneous presence of multiple particles in multiple excitation laser beams. Each time a cell passes through a focused laser spot (all lasers are amplitude modulated with unique frequencies or otherwise modulated so that they can be uniquely identified by the data acquisition system), the resulting pulse is analyzed for the presence of frequency components from all other excitation lasers (as signified by a DTFT magnitude at the modulation frequency of another excitation laser significantly above the signal background level). Unlike the first embodiment described hereinabove, where the DTFT was used to determine the emission for which quantification was desired, the present embodiment uses the computed DTFT values to correct the total emission measurement for the presence of any contaminating emissions.

Figure 9:
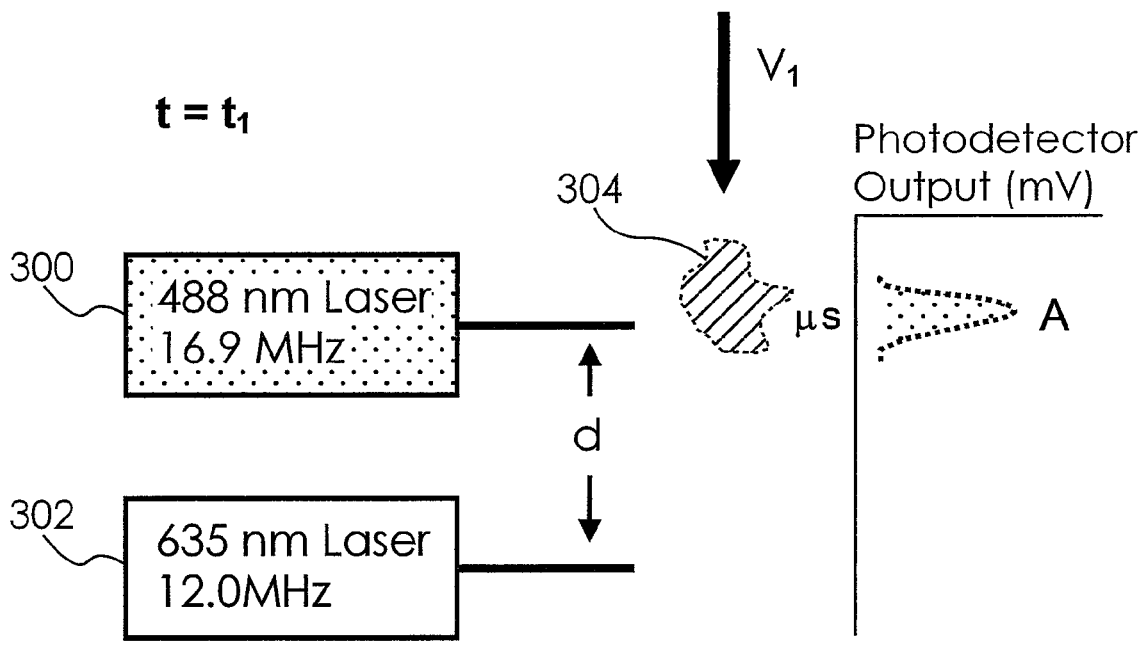
FIG. 9 is a schematic illustration of a single particle flowing through a flow cytometry system having two spatially separated lasers according to one embodiment disclosed herein.
Figure 9:
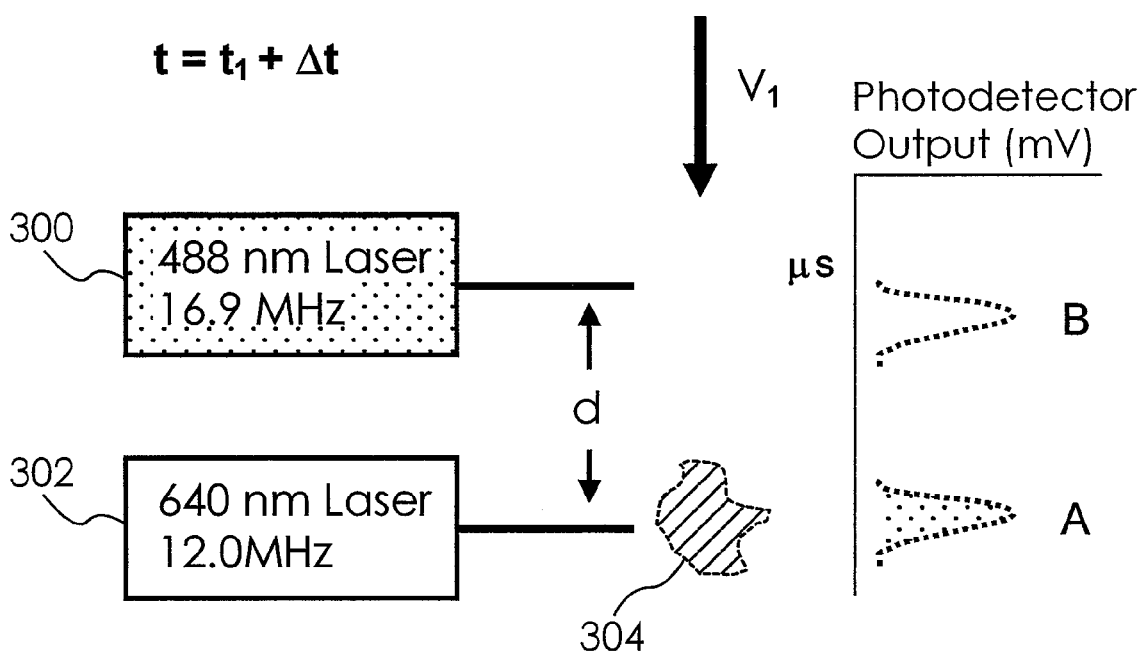

FIG. 9 schematically illustrates the response of a single photodetector, configured to measure the emission of both APC and PE-Cy5 labels on particles in a jetting stream or cuvette. The particles pass through successive laser focus spots comprising a 488 nm laser 300 modulated at 16.9 MHz and a 635 nm laser 302 modulated at 12.0 MHz. The laser 300 will excite the PE-Cy5 labels and the laser 302 will excite the APC labels. A bandpass filter (not shown) centered at 670 nm with a full width at half maximum (FWHM) transmission band of 40 nm is placed in front of the photodetector (not shown).

Shown in the upper portion of FIG. 9 (at time $t=t_1$) is a single cell 304 flowing in a stream at a constant velocity of $V_1$. The lasers 300 and 302 are separated by a distance d. If the cell 304 intersects with the 488 nm beam from laser 300 at time $t_1$ then it will intersect with the 640 nm beam from laser 302 at a time $t_2=t_1+\Delta t$, where $\Delta t=(V_1/d)^{-1}$. A photodetector output pulse is formed as the cell passes through the laser beam. Hence, a pulse A is formed as the cell 304 passes through the laser 300 focus spot. The photodetector output falls back to baseline before the cell 304 reaches the laser 302 focus spot, where its emission produces a pulse B in the photodetector output. Generally when the cell is centered in the laser beam spot, the highest rate of emission occurs, coinciding with the peak of the photodetector output pulse. In the present example, the two photodetector output pulses A and B are sufficiently separated in time such that they could easily be discriminated and independently measured by a data acquisition system.

Figure 10:
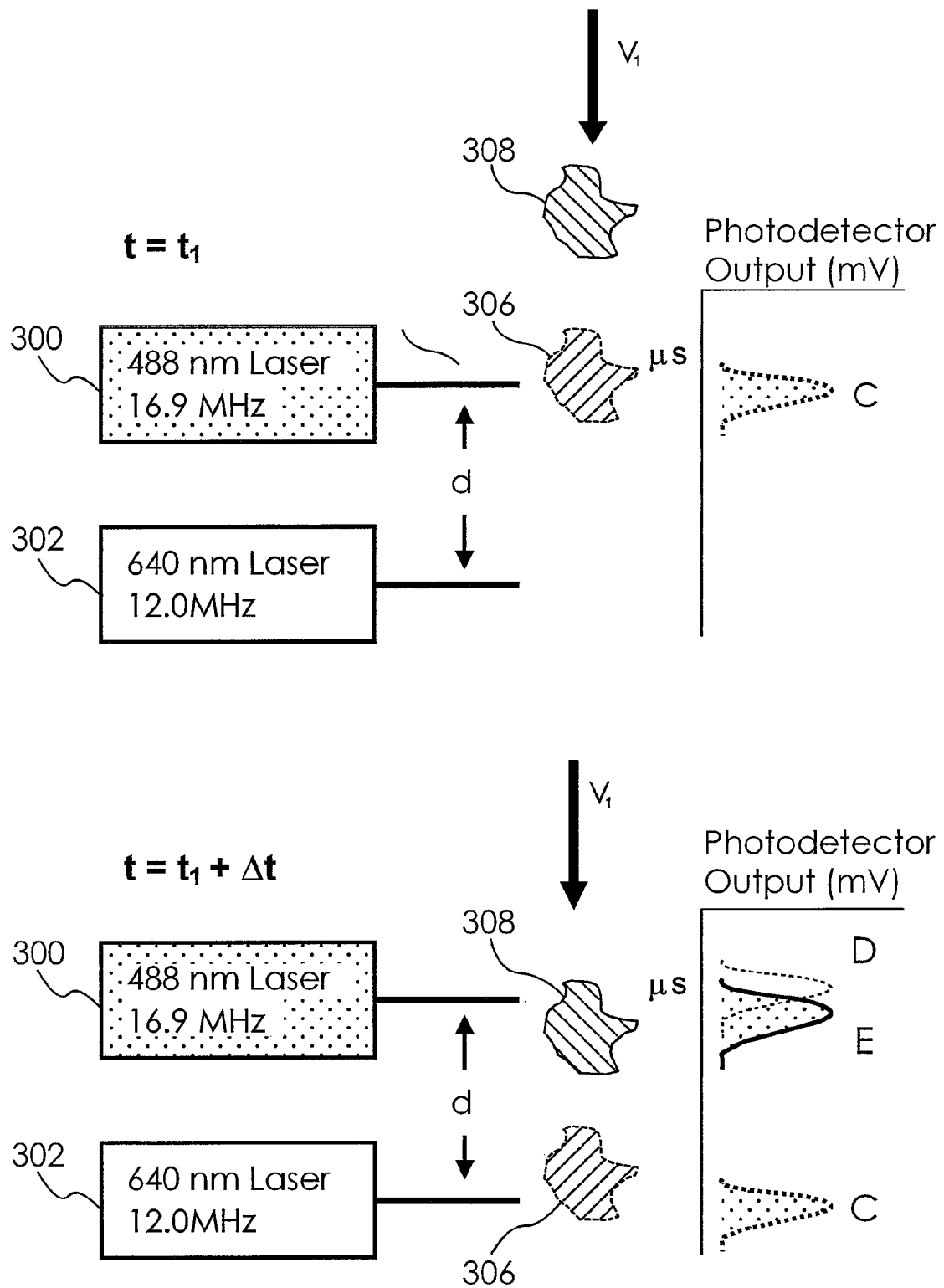
FIG. 10 is a schematic illustration of a two successive particles flowing through a flow cytometry system having two spatially separated lasers according to one embodiment disclosed herein.

FIG. 10 schematically illustrates the problem of inter-beam cell coincidence. In a flow cytometer, the cells arrive at the laser in single file, but the spacing between successive cells is random. This means that cells can be spaced such that multiple cells may be in separate laser beam spots at the same time. This is referred to as inter-beam coincidence.

In FIG. 10, the photodetector output pulse C is produced at time $t_1$ when the cell 306 passes through the 488 nm laser 300 spot. Photodetector output pulse D is produced by the cell 306 passing through the 640 nm laser 302 spot at time $t_1+\Delta t$. In this case, however, a second cell 308 has arrived in the 488 nm laser 300 spot at a time that coincides with $t_1+\Delta t$. The cell 308 produces output pulse E from the photodetector. If the data acquisition system can only measure pulse features like pulse peak, pulse height or pulse area, (as is the case for prior flow cytometry systems) there will be no way to distinguish between the emission produced by the cell 306 and the emission produced by the cell 308 at $t_2=t_1+\Delta t$. As discussed hereinabove, to address this problem, the prior art has used optical spatial filtering systems and separate optical detection paths. When using such a prior art system for the example of FIG. 10, two photodetectors would be utilized, each configured with the same bandpass optical filter. A spatial filter would be installed to limit the field of view for each photodetector to only a single laser beam focus spot. As previously mentioned, this method has the following problems:

1. Collection efficiency is reduced due to the presence of the spatial filtering system.
2. Laser beam focus spots must be aligned precisely to the points defined by the spatial filter.
3. A very limited number of beam focus spots (usually up to 3) can be aligned into a single collection optic. The focus spots that are off from the optical axis of the collection optic suffer from reduced collection efficiency.
4. The spatial filter approach requires duplication of all optical paths and elements for each separate laser beam spot, making it expensive and not scalable.
5. Measurements from different laser beam focus spots are not easily comparable because the emission passes through different optical elements and are registered on a different photodetector that varies in noise and gain characteristics.

The modulation system described herein provides an elegant solution to the problem of inter-beam coincidence. Since each laser's amplitude is modulated at a distinct frequency, all fluorescent emission will also be modulated at the modulation frequency of the source excitation laser. It should be understood that some parameters of the emission waveform, such as modulation depth and phase, will be functions of the emission lifetime of the fluorophore. However, as long as the period of the excitation modulation is much less than the fluorescence lifetime (true for all probes commonly used in flow cytometry) then the emission frequency will match the excitation frequency. Using this method, all emission components carry a unique signature of the excitation laser that produced them.

For the case of the inter-beam coincidence shown in FIG. 10, a standard pulse area measurement is made for pulse C and for the combined pulse resulting from D+E. In addition to the standard pulse area measurement, the DTFT is calculated for all pulses at 12 MHz and 16.9 MHz (the modulation frequencies). The combined pulse D+E will have frequency components from both of the lasers 300 and 302. Because pulse E was produced by excitation from the 488 nm laser 300, it will contribute power at the 16.9 MHz modulation frequency of laser 300. Pulse D was produced by excitation from the 640 nm laser 302, so its power will be at the 12 MHz modulation frequency of laser 302. The total area ($A_{tot}$) of the combined D+E pulse is given by:

$$A_{tot}=A_D+A_E$$

$$A_D=C_1*DTFT(12\text{ MHz})$$

$$A_E=C_2*DTFT(16.9\text{ MHz})$$

Where C1 and C2 are empirically determined constants.

Figure 11:
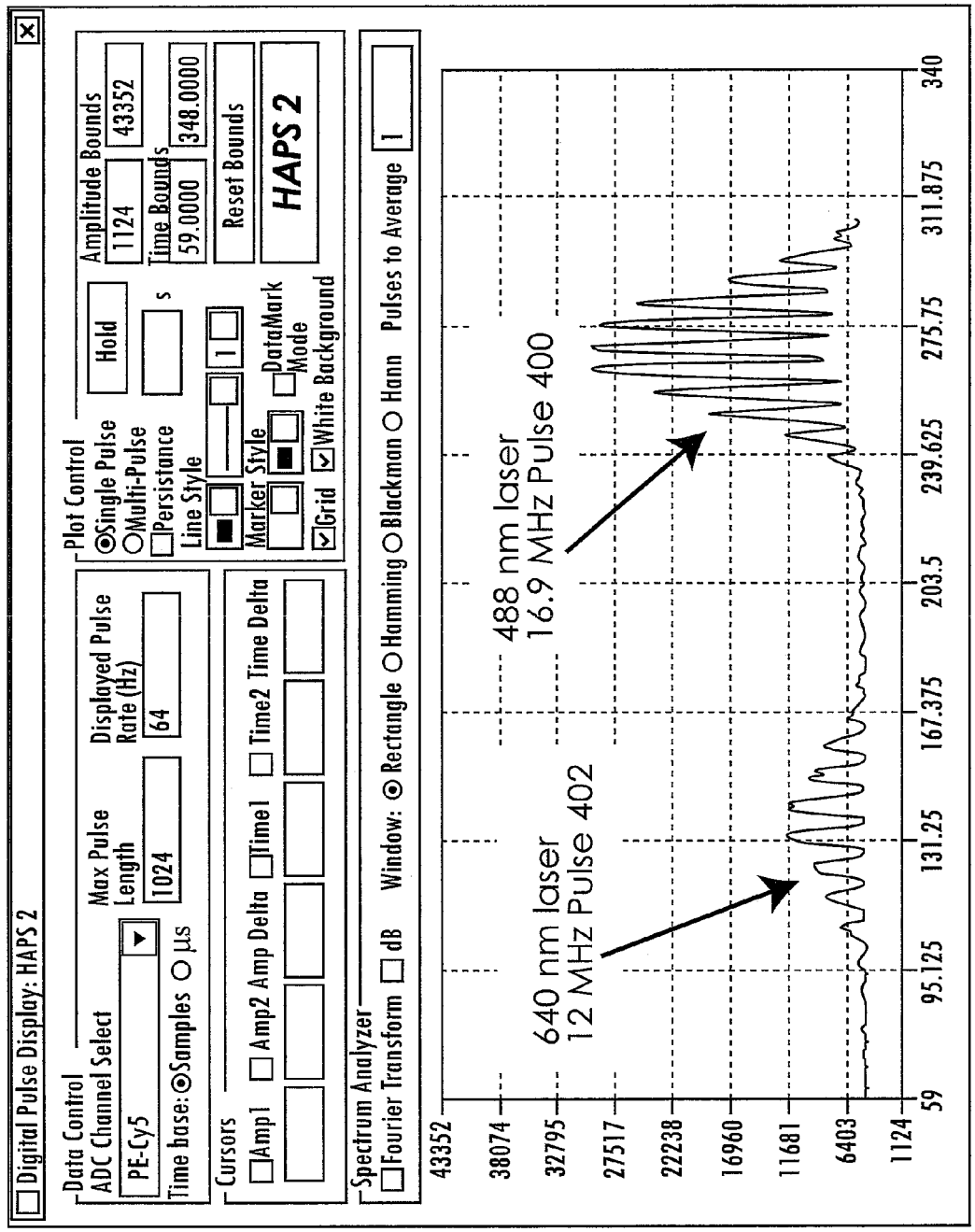
FIG. 11 is a display of a pulse output from a flow cytometer when the scenario illustrated in FIG. 9 occurs.

Referring now to FIG. 11, there is illustrated a display of the digitally sampled data the pulses A and B from FIG. 9 as collected on a flow cytometer. The display shows the output of a 40 MHz bandwidth PMT as the single particle 304 labeled with both APC and PE-Cy5 passed through both of the laser beam 300 and 302 focus spots. The particle 304 first passed through the 488 nm laser 300 which was modulated at 16.9 MHz (pulse envelope 400 on the right) and then passed through the 640 nm laser 302 which was modulated at 12 MHz (pulse envelope 402 on the left). Both of the pulses 400 and 402 contain emission spectra from only the single associated excitation source 300 or 302, as can be verified by analysis of the pulses using DTFT or similar techniques.

Figure 12:
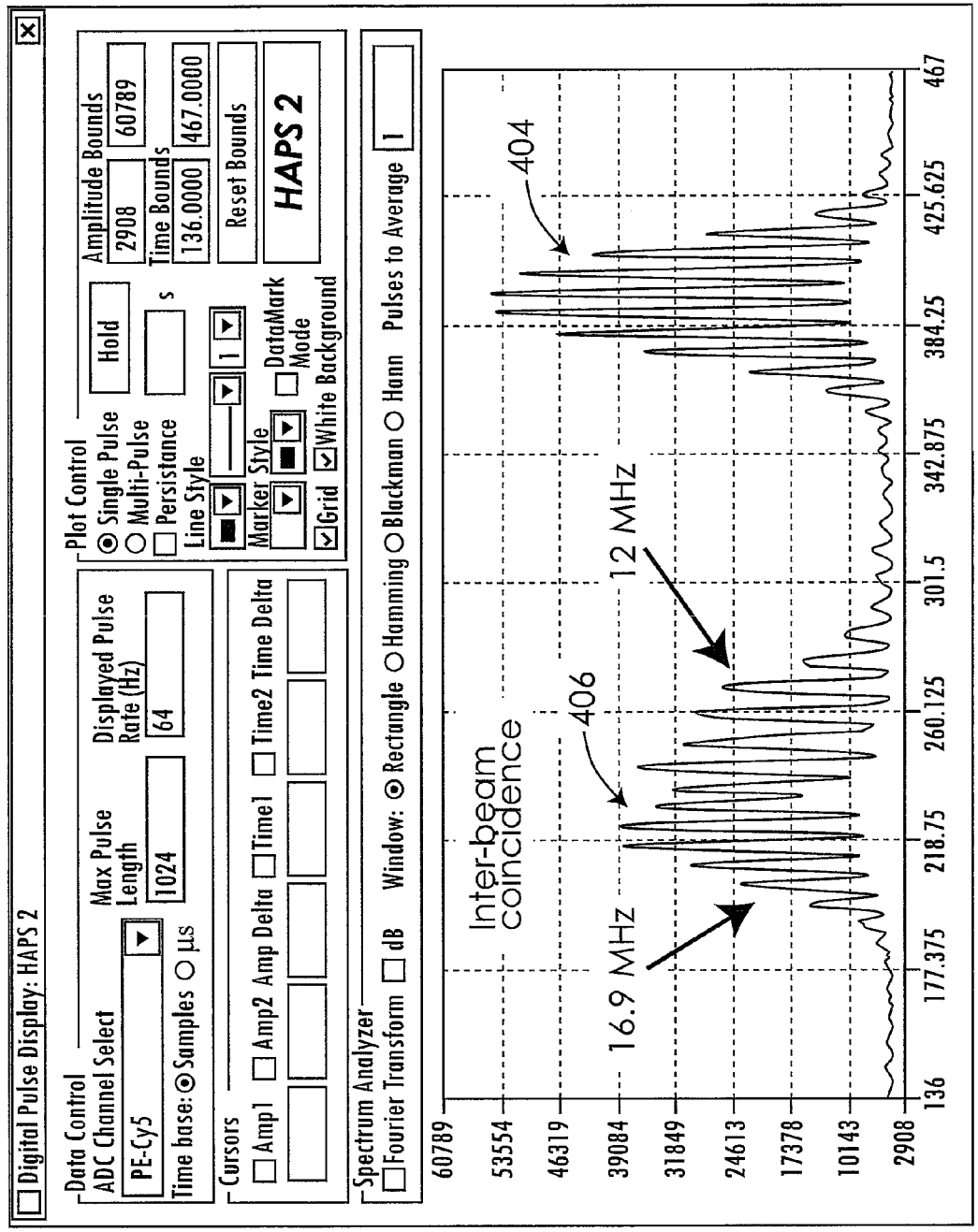
FIG. 12 is a display of a pulse output from a flow cytometer when the scenario illustrated in FIG. 10 occurs.

FIG. 12 illustrates a display of the digitally sampled data the pulses C and D+E from FIG. 10 as collected on a flow cytometer. This data illustrates the case of an actual inter-beam coincidence event. The display of FIG. 12 again shows the output of a 40 MHz bandwidth PMT, but this time the output is reflective of the passage of closely spaced particles 306 and 308 (both labeled with both APC and PE-Cy5) passing through both of the laser beam 300 and 302 focus spots. The particle 306 first passed through the 488 nm laser 300 which was modulated at 16.9 MHz (pulse envelope 404 on the right) and then passed through the 640 nm laser 302 which was modulated at 12 MHz (pulse envelope 406 on the left). While particle 306 was still emitting fluorescence caused by excitation by the laser 302, particle 308 has entered the laser 300 focus spot and its fluorescent emission is also contributing to the formation of the output pulse envelope 406. The pulse envelope 406 is broadened compared to the single particle pulse envelope 402 of FIG. 11 and the contribution from the two different modulation frequencies (12 MHz and 16.9 MHz) can clearly be seen in the waveform. One can infer that the first particle passed cleanly through the 488 nm laser 300, but while it was in the 640 nm laser 302 spot, the second particle entered the 488 nm laser 300 spot.

Figure 13:
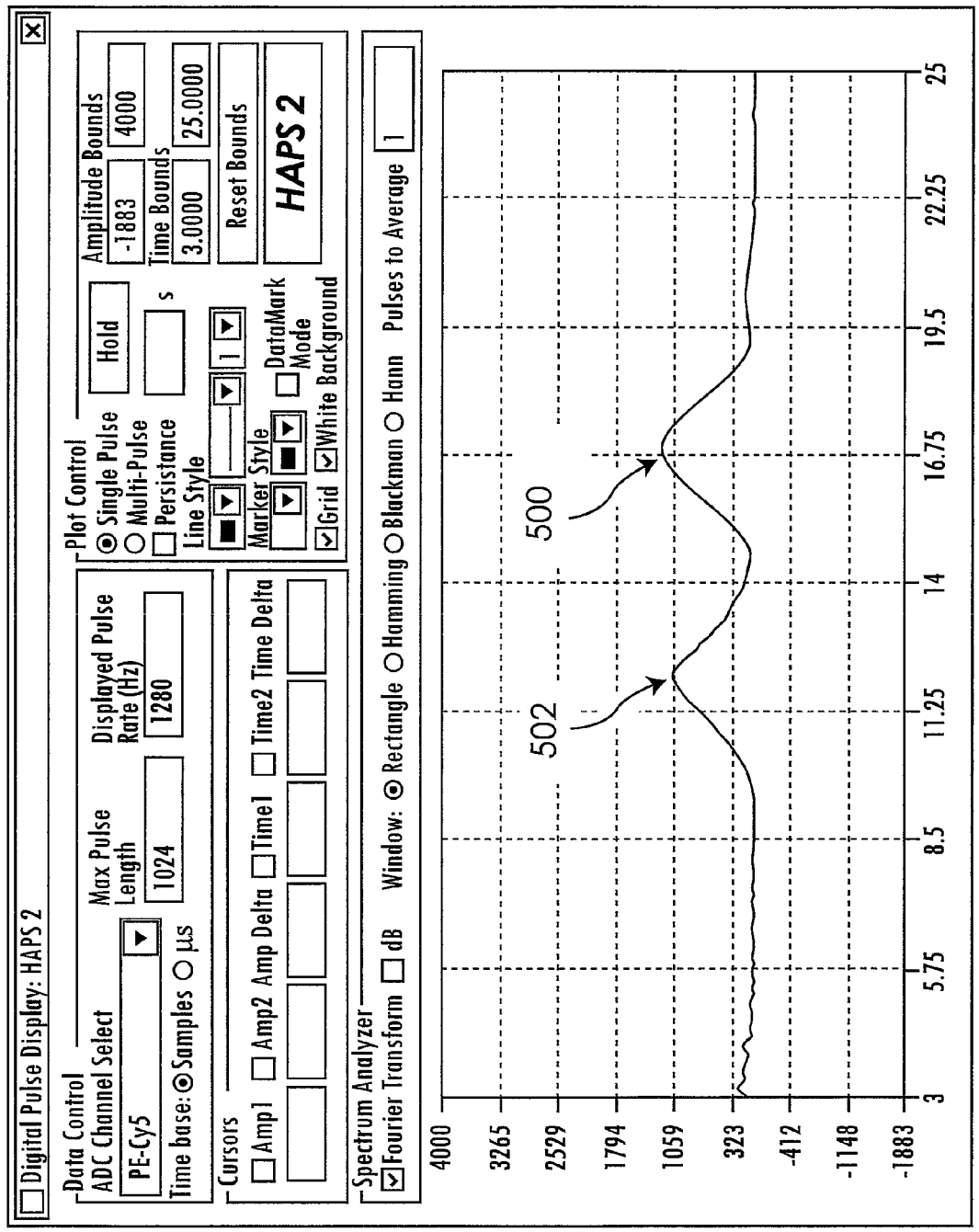
FIG. 13 is a display of a Fast Fourier Transform of the pulse data from FIG. 12.

FIG. 13 illustrates an FFT calculated for the pulse 406. This is the frequency spectrum that is seen when inter-beam coincidence occurs. Because the data of FIG. 13 was calculated off-line for illustration purposes, an FFT was used. As discussed hereinabove, to enable real-time measurement, the DTFT is calculated by the DSP processor only at the specific laser modulation frequencies. The points in the FFT spectrum where the DTFT values are calculated for the case of a 488 nm laser modulated at 16.9 MHz (point 500) and a 640 nm laser modulated at 12 MHz (point 502) are indicated in the figure. The magnitude of the DTFT is proportional to the temporal pulse area.

The total fluorescence emission produced by each laser's excitation is given by:

$$A_{488}=C_1*DTFT(16.9\ MHz)$$

$$A_{640}=C_2*DTFT(12\ MHz)$$

Where C1 and C2 are constants that are determined through instrument calibration.

FIG. 14 shows data collected on a flow cytometer utilizing the modulation methods described hereinabove. FIG. 14 shows how traditional pulse area measurements are corrected using the embodiments disclosed herein and how the constants C1 and C2 are determined empirically. The data shown in FIG. 14 were collected from particles co-labeled with APC and PE-Cy5. Data were collected using a single photodetector with no spatial filtering. A bandpass filter centered at 670 nm with a FWHM transmission of 40 nm was used to select the correct emission band. FIGS. 14A-C consist of scatter plots of the total pulse area measured from the 488 nm laser 300 ($A_C$ or $A_E$ in the example of FIG. 10) on the x-axis and the magnitude of the DTFT for the 640 nm laser 302 frequency (DTFT (12 MHz)) on the y-axis. FIGS. 14D-F are histograms of the total pulse area where fluorescence intensity is on the x-axis and the number of particles is on the y-axis.

In FIGS. 14A and 14D, the 488 nm laser 300 is on and the 640 nm laser 302 is turned off. As expected, FIG. 14A shows that the magnitude of the DTFT (12 MHz) for the 640 nm laser 302 (i.e. the y-axis dimension) is near zero. The associated histogram of FIG. 14D shows a single distribution.

In FIGS. 14B and 14E, the 488 nm laser 300 remains on and the 640 nm laser 302 has also been turned on. It is now possible to see the effect of inter-beam coincidence. We see that the DTFT (12 MHz) values are highly correlated with the Pe-Cy5 area, but are widely distributed. Since the separation between successive particles is a random Poisson-distributed variable, inter-beam coincidence occurs in a Poisson-distributed fashion. The probability distribution for inter-beam coincidence is a function of beam spot size, particle velocity and particle size. Regardless of the specific parameters of the distribution, the frequency of inter-beam coincidence will increase as the average particle rate increases. The error or contaminating effect of inter-beam coincidence can be seen clearly in both the scatter plot (FIG. 14B) and the associated histogram (FIG. 14E).

Using these data, there are at least two ways to deal with the error introduced by inter-bean coincidence. It should be noted that correction of the emission measurement is not necessarily required. The DTFT method of the present embodiment is a very sensitive measurement of inter-beam, spectral contamination. Once this is detected it is also possible to simply ignore, or gate out, data from particles whose measurements were contaminated by the presence of other particles. One could simply program the computer to ignore all contaminated measurements by using the scatter plot to gate out the data that includes inter-beam coincidence. This "gating" approach may be the preferred approach in an analysis situation. However, this may be undesirable when cell sorting, as the gating process will reduce the yield of the sorting experiment.

Alternatively, FIGS. 14C and 14F illustrate how the total pulse area data can be corrected. The emission specific to Pe-Cy5 fluorescence emission resulting from the 488 nm laser excitation ($A_E$) is calculated by correcting the total area measured ($A_{tot}$) for the inter-beam coincident APC emission resulting from the 640 nm laser excitation ($A_D$) as shown below.

$$A_E=A_{tot}-A_D$$

$$A_E=A_{tot}-C_2*DTFT(12\ MHz)$$

The constant $C_2$ is determined empirically by running a control sample and increasing the magnitude of $C_2$ until there is no longer correlation between the magnitude of DTFT (12 MHz) and the total PE-Cy5 area. Essentially, any contribution to the pulse area from the 640 nm laser 302 is subtracted out of the total pulse area so that only the emission component from the 488 nm laser 300 remains This method offers the following benefits in a flow cytometry system:

1. Since inter-beam coincidence occurs relatively infrequently, the majority of total area measurements are unaffected (i.e. DTFT (12 MHz)<<$A_{tot}$ so only a small number of pulses (measurements) must be corrected. The expected rate of events needing correction can be modeled using Poisson statistics based on the dwell time in each laser beam, the average particle arrival rate, and the average particle size.
2. The method, therefore, provides all the benefits of the traditional pulse area measurements without the need for the additional cost and complexity of the spatially filtered optical systems.
3. A lower minimum detection point, achieved by computation of the total emission by direct summing of the ADC samples comprising the pulse, can be maintained.
4. The method easily scales to many laser beam focus spots. In fact, spots can be placed much closer together than when spatial filtering is used. This is because the emission pulses are Gaussian in nature (due to Gaussian beam waist profiles) and spatial filters must be placed far enough apart to ensure that the emission pulse for the largest particle returns to within >99% to baseline. The modulation system can allow overlapping of the pulse edges or fringes since correction for any overlap is applied.
5. The main reason for using separated beams is to make the full dynamic range of the photodetector (typically $10^4$) available for each particle/laser intersection. The only case where the full dynamic range is not available is when multiple particles are simultaneously present in multiple focused excitation laser beams. If full dynamic range is necessary for the measurement, the present embodiment detects such contamination and allows these data to be ignored or corrected. If the dynamic range of the sample is much less than the full dynamic range of the photodetector (for example $10^2$), then it is possible to maintain the lasers collinear and perform the measurements using only the DTFT magnitudes. This method offers additional information (i.e. the DTFT values) while preserving all of the traditional pulse feature measurements. The methods disclosed herein therefore offers significant flexibility to the user with regard to experimental design.

The modified technique of the present embodiment allows the use of separated excitation laser beam focus spots without the need for completely separate detection paths and the complexity and negative performance impact of spatial filtering (as used on prior art flow cytometers). This allows a single detector (and associated optical filters) to be multiplexed for use with many excitation lasers, providing a significant cost savings and reduction in size.

The embodiments described hereinabove can be used in a variety of combinations. Completely collinear beams can be used if dynamic range and minimum detection are not an issue for a particular application. Alternatively, some excitation lasers can be collinear and others separately focused based upon their potential to produce overlapping spectral emissions. This flexible approach allows many more excitation lasers to be employed simultaneously on a flow cytometer without complicating the detection and data processing sections of the equipment.

The systems and methods described hereinabove solve many of the problems associated with the use of spatially separating laser beams on flow cytometers, such as:
1. A single excitation laser focus spot simplifies alignment and decreases the measurement dwell time of the system (i.e. the time particles or cells are in the laser focus spot).
2. All "crosstalk" between excitation lasers is eliminated more effectively than with spatial filters and without the potential attendant loss of fluorescent light.
3. A single photodetector can be used to measure emission produced by numerous excitation sources.
4. The excitation laser focus spot can be located in the center, or optimum focus, of the collection optic.
5. Any number of excitation lasers can be used simultaneously. The limit is determined by the minimum achievable bandwidth of the modulation of the detected signal—modulation frequencies must be separated such that the peaks as seen in the PSD of FIG. 6 do not overlap.

The analysis method is well suited for implementation into any flow cytometer DSP system. DSP hardware is specifically designed for efficient performance of Fourier analyses such as that described above. Further, it may be noted that it is unnecessary to compute the energy content of the signal at all frequencies (up to the Nyquist rate)—all that is needed is the magnitude of the Fourier transform at the specific excitation laser modulation frequencies of interest. Thus rather than performing a computationally expensive Discrete Fourier Transform (DFT) or the somewhat more efficient implementation of this algorithm, known as the Fast Fourier Transform (FFT), the much more computationally efficient Discrete Time Fourier Transform (DTFT) may be computed for each frequency, making it possible to obtain the needed information in a maximum of a few microseconds. This means the process can be used for real-time cell sorting applications.

In view of the foregoing, and while the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:
1. A flow cytometer for measuring fluorescent emission from a particle, the flow cytometer comprising:
   a first excitation light source producing a first modulated excitation beam modulated at a first frequency;
   a second excitation light source producing a second modulated excitation beam modulated at a second frequency, said second frequency being different than said first frequency;
   beam combining optics adapted to receive said first and second modulated excitation beams and produce a combined modulated excitation beam;
   a single detector adapted to measure fluorescent emission from said particle when said particle is within said combined modulated excitation beam, said single detector producing a single detector output signal; and
   a signal processor operatively coupled to said single detector for receipt of said single detector output signal, said signal processor operative to use said first frequency and said second frequency to distinguish a first portion of said single detector output signal caused by excitation of said particle by said first modulated excitation beam and a second portion of said single detector output signal caused by excitation of said particle by said second modulated excitation beam even when said first portion and said second portion overlap temporally.

2. The flow cytometer of claim 1, wherein said first and second excitation light sources comprise first and second lasers.

3. The flow cytometer of claim 1, wherein said first modulated excitation beam is amplitude modulated at said first frequency and said second modulated excitation beam is amplitude modulated at said second frequency.

4. The flow cytometer of claim 1, wherein said first and second excitation light sources include respective first and second modulation power sources.

5. The flow cytometer of claim 1, wherein said first and second excitation light sources include respective first and second electro-optic modulators.

6. The flow cytometer of claim 1, wherein said single detector comprises a photomultiplier tube.

7. The flow cytometer of claim 6, wherein said single detector output signal comprises an analog signal.

8. The flow cytometer of claim 1, further comprising:
   an analog-to-digital converter operatively coupled to the single detector for receipt of said single detector output signal, said analog-to-digital converter producing a digitized detector output signal representative of said single detector output signal;
   wherein said signal processor receives said digitized detector output signal.

9. The flow cytometer of claim 1, wherein said signal processor is operative to perform a Fourier transform on said single detector output signal in order to distinguish said first and second portions.

10. The flow cytometer of claim 1, wherein said beam combining optics comprises a dichroic filter.

11. A flow cytometer for measuring fluorescent emission from a particle, the flow cytometer comprising:
   a first excitation light source producing a first modulated excitation beam modulated at a first frequency;
   a second excitation light source producing a second modulated excitation beam modulated at a second frequency, said second frequency being different than said first frequency;
   wherein said first modulated excitation beam and said second modulated excitation beam are produced at the same time;
   first optics adapted to focus said first modulated excitation beam at a first focus spot;

second optics adapted to focus said second modulated excitation beam at a second focus spot, said second focus spot being spatially separated from said first focus spot;

a single detector adapted to measure fluorescent emission from said particle when said particle is within either said first focus spot or said second focus spot, said single detector producing a single detector output signal; and a signal processor operatively coupled to said single detector for receipt of said single detector output signal, said signal processor operative to use said first frequency and said second frequency to distinguish a first portion of said single detector output signal caused by excitation of said particle by said first modulated excitation beam and a second portion of said single detector output signal caused by excitation of said particle by said second modulated excitation beam.

12. The flow cytometer of claim 11, wherein said first and second excitation light sources comprise first and second lasers.

13. The flow cytometer of claim 11, wherein said first modulated excitation beam is amplitude modulated at said first frequency and said second modulated excitation beam is amplitude modulated at said second frequency.

14. The flow cytometer of claim 11, wherein said first and second excitation light sources include respective first and second modulation power sources.

15. The flow cytometer of claim 11, wherein said first and second excitation light sources include respective first and second electro-optic modulators.

16. The flow cytometer of claim 11, wherein said single detector comprises a photomultiplier tube.

17. The flow cytometer of claim 16, wherein said single detector output signal comprises an analog signal.

18. The flow cytometer of claim 11, further comprising:
an analog-to-digital converter operatively coupled to said single detector for receipt of said single detector output signal, said analog-to-digital converter producing a digitized detector output signal representative of said single detector output signal;
wherein said signal processor receives said digitized detector output signal.

19. The flow cytometer of claim 11, wherein said signal processor is operative to perform a Fourier transform on said single detector output signal in order to distinguish said first and second portions.

20. A flow cytometer for measuring fluorescent emission from a particle, the flow cytometer comprising:
a first excitation light source producing a first modulated excitation beam modulated at a first frequency;
a second excitation light source producing a second modulated excitation beam modulated at a second frequency, said second frequency being different than said first frequency;
wherein said first modulated excitation beam and said second modulated excitation beam are produced at the same time;
first optics adapted to focus said first modulated excitation beam at a first focus spot;
second optics adapted to focus said second modulated excitation beam at a second focus spot, said second focus spot being spatially separated from said first focus spot;
a single detector adapted to measure fluorescent emission from said particle when said particle is within either said first focus spot or said second focus spot, said single detector producing a single detector output signal; and a signal processor operatively coupled to said single detector for receipt of said single detector output signal, said signal processor operative to use said first frequency and said second frequency to distinguish a first portion of said single detector output signal caused by excitation of said particle by said first modulated excitation beam and a second portion of said single detector output signal caused by excitation of said particle by said second modulated excitation beam, said signal processor further operable to correct said single detector output signal for the effects of inter-beam coincidence.

21. The flow cytometer of claim 20, wherein said correction comprises gating out portions of said detector output signal containing inter-beam coincidence.

22. The flow cytometer of claim 20, wherein said correction comprises removing a portion of the detector output signal attributable to fluorescence excited by said first excitation light source.

23. The flow cytometer of claim 22, wherein said correction comprises calculating a pulse area according to:
$$A_{PULSE} = A_{tot} - C2 * DTFT(\text{said first modulation frequency}),$$
where $A_{tot}$ is a total pulse area and C2 is a constant.

24. The flow cytometer of claim 20, wherein said first and second excitation light sources comprise first and second lasers.

25. The flow cytometer of claim 20, wherein said first modulated excitation beam is amplitude modulated at said first frequency and said second modulated excitation beam is amplitude modulated at said second frequency.

26. The flow cytometer of claim 20, wherein said first and second excitation light sources include respective first and second modulation power sources.

27. The flow cytometer of claim 20, wherein said first and second excitation light sources include respective first and second electro-optic modulators.

28. The flow cytometer of claim 20, wherein said single detector comprises a photomultiplier tube.

29. The flow cytometer of claim 28, wherein said single detector output signal comprises an analog signal.

30. The flow cytometer of claim 20, further comprising:
an analog-to-digital converter operatively coupled to said single detector for receipt of said single detector output signal, said analog-to-digital converter producing a digitized detector output signal representative of said single detector output signal;
wherein said signal processor receives said digitized detector output signal.

31. The flow cytometer of claim 20, wherein said signal processor is operative to perform a Fourier transform on said single detector output signal in order to distinguish said first and second portions.

32. A flow cytometer for measuring fluorescent emission from a particle, the flow cytometer comprising:
a first excitation light source producing a first modulated excitation beam modulated at a first frequency;
a second excitation light source producing a second modulated excitation beam modulated at a second frequency, said second frequency being different than said first frequency;
beam combining optics adapted to receive said first and second modulated excitation beams and produce a combined modulated excitation beam;
a detector adapted to measure fluorescent emission from said particle when said particle is within said combined modulated excitation beam, said detector producing a detector output signal; and a signal processor operatively coupled to said detector for receipt of said detector output signal, said signal processor operative to distinguish a first portion of said detector output signal caused by excitation of said particle by said first modulated excitation beam and a second portion of said detector output signal caused by excitation of said particle by said second modulated excitation beam.

33. A flow cytometer for measuring fluorescent emission from a particle, the flow cytometer comprising:
- a first excitation light source producing a first modulated excitation beam modulated at a first frequency;
- a second excitation light source producing a second modulated excitation beam modulated at a second frequency, said second frequency being different than said first frequency;
- first optics adapted to focus said first modulated excitation beam at a first focus spot;
- second optics adapted to focus said second modulated excitation beam at a second focus spot, said second focus spot being spatially separated from said first focus spot;
- a detector adapted to measure fluorescent emission from said particle when said particle is within either said first focus spot or said second focus spot, said detector producing a detector output signal; and
- a signal processor operatively coupled to said detector for receipt of said detector output signal, said signal processor operative to distinguish a first portion of said detector output signal caused by excitation of said particle by said first modulated excitation beam and a second portion of said detector output signal caused by excitation of said particle by said second modulated excitation beam.

34. A flow cytometer for measuring fluorescent emission from a particle, the flow cytometer comprising:
- a first excitation light source producing a first modulated excitation beam modulated at a first frequency;
- a second excitation light source producing a second modulated excitation beam modulated at a second frequency, said second frequency being different than said first frequency;
- wherein said first modulated excitation beam and said second modulated excitation beam are produced at the same time;
- first optics adapted to focus said first modulated excitation beam at a first focus spot;
- second optics adapted to focus said second modulated excitation beam at a second focus spot, said second focus spot being spatially separated from said first focus spot;
- a detector adapted to measure fluorescent emission from said particle when said particle is within either said first focus spot or said second focus spot, said detector producing a detector output signal; and
- a signal processor operatively coupled to said detector for receipt of said detector output signal, said signal processor operative to distinguish a first portion of said detector output signal caused by excitation of said particle by said first modulated excitation beam and a second portion of said detector output signal caused by excitation of said particle by said second modulated excitation beam, said signal processor further operable to correct said detector output signal for the effects of inter-beam coincidence.

* * * * *